United States Patent
Armstrong et al.

(12)

(10) Patent No.: US 6,603,061 B1
(45) Date of Patent: Aug. 5, 2003

(54) AGROBACTERIUM-MEDIATED PLANT TRANSFORMATION METHOD

(75) Inventors: Charles L Armstrong, St. Charles, MO (US); Jyoti R Rout, Middleton, WI (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/364,254

(22) Filed: Jul. 29, 1999

(51) Int. Cl.$^7$ .................. C12N 15/84; C12N 15/82; A01H 1/00; A01H 4/00
(52) U.S. Cl. ................. 800/294; 800/278; 800/312; 800/314; 800/306; 800/320.1; 800/322; 435/468; 435/469; 435/419; 435/426; 435/427; 435/428; 435/424; 435/430; 435/431
(58) Field of Search .................. 800/298, 278, 800/294, 312, 314, 320, 320.1, 320.2, 320.3, 322, 306; 435/468, 469, 410, 412, 415, 416, 419, 431, 429, 424, 427, 428, 430

(56) References Cited

FOREIGN PATENT DOCUMENTS

| WO | WO 9534667 A2 | 12/1995 |
|---|---|---|
| WO | WO 9832326 A2 | 7/1998 |
| WO | WO 9854961 A2 | 12/1998 |
| WO | WO 991449 A1 | 3/1999 |

OTHER PUBLICATIONS

Hansen et al., Recent advance in the transformation of plants, Jun. 1999, vol. 4, No. 6, pp. 226–231.*
Wilson et al., Botany: Fifth Edition, 1971, Holt, Rinehast and Wiston, p. 713 and p. 101.*
Grevelding et al, Single–copy T–DNA insertions in Arabidopsis are the predominant form of integration in root–derived transgenics, whereas multiple insertions ar found in leaf discs. Plant Mol. Biol. 23:847–860, 1993.*
Enriquez–Obregon et al, Genetic transformation of sugarcane by Agrobacterium tumefaciens using antioxidant compounds. Biotecnologia Aplicada 14:169–174, 1997.*
Paszkowski J et al, "Expression in Transgenic Tobacco of the Bacterial Neomycin Phosphotransferase Gene Modified Intron Insertions of Various Sizes," Plant Molecular Biology, vol. 19 (No. 5), p. 825–36, (Feb. 8, 1992).

* cited by examiner

*Primary Examiner*—David T. Fox
*Assistant Examiner*—David H Kruse

(57) ABSTRACT

The present invention relates to a novel transformation system for generating transformed plants with lower copy inserts and improved transformation efficiency. In particular, the invention relates to the use of Agrobacterium growth inhibiting agents during the Agrobacterium-mediated transformation process that suppress Agrobacterium growth and reduce T-DNA transfer to the target plant genome.

6 Claims, 5 Drawing Sheets

ND PLANT
AGROBACTERIUM-MEDIATED PLANT TRANSFORMATION METHOD

BACKGROUND OF THE INVENTION

The present invention relates to the field of plant biotechnology. More specifically, it concerns methods of incorporating genetic components into a plant comprising a T-DNA transfer process. In particular, provided herein are systems for genetically transforming monocotyledonous plants including corn, rice, and wheat.

The method comprises novel conditions during the inoculation, co-culture, or infiltration of Agrobacterium with a transformable plant cell or tissue. Exemplary methods include an improved method using a bacterial growth suppressing agent during the Agrobacterium-mediated transformation process. The improved method can be used for introducing nucleic acids into transformable cells or tissues using a variety of selectable and/or screenable marker systems, and with a number of different plant species. The present invention also provides transgenic plants, in particular, corn, rice, and wheat. In other aspects, the invention relates to the production of stably transformed plants, gametes, and offspring from these plants.

During the past decade, it has become possible to transfer genes from a wide range of organisms to crop plants by recombinant DNA technology. This advance has provided enormous opportunities to improve plant resistance to pests, disease and herbicides, and to modify biosynthetic processes to change the quality of plant products (Knutson et al., 1992; Piorer et al., 1992). However, the availability of efficient Agrobacterium-mediated transformation methods suitable for high capacity production of economically important plants is limited. In particular, a novel culture system that generates reproducible transformants with a simple integration pattern of the introduced DNA into the host genome, more specifically, the integration of a low copy number (one to two copies) of the introduced DNA is needed.

There have been many methods attempted for plant transformation, but only a few methods are highly efficient. Moreover, few methods are both highly efficient and result in transformants with simple integration pattern and low copy number of the introduced DNA. Copy number refers to the number of complete or incomplete copies of T-DNA introduced in host cell. The technologies for the introduction of DNA into cells are well known to those of skill in the art and can be divided into categories including but not limited to: (1) chemical methods (Graham and van der Eb, 1973); (2) physical methods such as microinjection (Capecchi, 1980), electroporation ( Fromm et al., 1985; U.S. Pat. No. 5,384,253) and the gene gun (Christou, 1992; Fynan et al., 1993); (3) viral vectors (Clapp, 1993; Lu et al., 1993; Eglitis and Anderson, 1988);(4) receptor-mediated mechanisms (Curiel et al., 1992); and (5) Agrobacterium-mediated plant transformation methods.

Until recently, the methods employed for some monocot species included direct DNA transfer into isolated protoplasts and microprojectile-mediated DNA delivery (Fromm et al, 1990). The protoplast methods have been widely used in rice, where DNA is delivered to the protoplasts through liposomes, PEG, and electroporation. While a large number of transgenic plants have been recovered in several laboratories (Datta et al., 1990), the protoplast methods require the establishment of long-term embryogenic suspension cultures. Some regenerants from protoplasts are infertile and phenotypically abnormal due to the long-term suspension culture (Davey et al., 1991; Rhodes et.al.,1988). U.S. Pat. No. 5,631,152 describes a rapid and efficient microprojectile bombardment method for the transformation and regeneration of monocots and dicots.

To date, microparticle- and Agrobacterium-mediated gene delivery are the two most commonly used plant transformation methods. Microparticle-mediated transformation refers to the delivery of DNA coated onto microparticles that are propelled into target tissues by several methods. This method can result in transgenic events with a higher copy number, complex integration patterns, and fragmented inserts. Agrobactenum-mediated plant transformation can also result in transformed plants with multiple copies of inserts and complex integration patterns. A reduction in copy number can result from a decrease in the frequency of T-DNA transfer. Accordingly, novel culture conditions can be manipulated to impact the frequency of T-DNA transfer and can produce transformation events containing the optimum number of copies of the introduced DNA.

A reproducible Agrobacterium-mediated method that consistently results in low copy number inserts and is applicable to a broad number of plant species is desirable for a number of reasons. For example, the presence of multiple inserts can lead to a phenomenon known as gene silencing which can occur by several mechanisms including but not limited to recombination between the multiple copies which can lead to subsequent gene loss. Also, multiple copies can cause reduced levels of expression of the gene which in turn can result in the reduction of the characteristic(s) conferred by the gene product(s). Despite the number of transformation methods available for specific plant systems, it would be advantageous to have a method of introducing genes into plants that is applicable to various crops and a variety of transformable tissues.

Agrobacterium-mediated transformation is achieved through the use of a genetically engineered soil bacterium belonging to the genus Agrobacterium. Several Agrobacterium species mediate the transfer of a specific DNA known as "T-DNA", that can be genetically engineered to carry any desired piece of DNA into many plant species. The major events marking the process of T-DNA mediated pathogenesis are: induction of virulence genes, processing and transfer of T-DNA, This process is the subject of many reviews (Ream, 1989; Howard and Citovsky, 1990; Kado, 1991; Hooykaas and Schilperoort, 1992; Winnans, 1992; Zambryski, 1992; Gelvin, 1993; Binns and Howitz, 1994; Hooykaas and Beijersbergen 1994; Lessl and Lanka, 1994; Zupan and Zambryski, 1995).

Agrobacterium-mediated genetic transformation of plants involves several steps. The first step, in which the Agrobacterium and plant cells are first brought into contact with each other, is generally called "inoculation". Following the inoculation step, the Agrobacterium and plant cells/tissues are usually grown together for a period of several hours to several days or more under conditions suitable for growth and T-DNA transfer. This step is termed "co-culture". Following co-culture and T-DNA delivery, the plant cells are often treated with bacteriocidal and-or bacteriostatic agents to kill the Agrobacterium. If this is done in the absence of any selective agents to promote preferential growth of transgenic versus non-transgenic plant cells, then this is typically referred to as the "delay" step. If done in the presence of selective pressure favoring tranasgenic plant cells, then it is referred to as a "selection" step. When a "delay" is used, it is followed by one or more "selection" steps. Both the "delay" and "selection". steps typically include bacteriocidal and-or bacteriostatic agents to kill any remaining Agrobacterium cells because the growth of Agrobacterium cells is undesirable after the infection (inoculation and co-culture) process.

Although transgenic plants produced through Agrobacterium-mediated transformation generally contain a simple integration pattern as compared to microparticle-mediated genetic transformation, a wide variation in copy number and insertion patterns exists (Jones et al, 1987; Jorgensen et al., 1987). Moreover, even within a single plant genotype, different patterns of T-DNA integration are possible based on the type of explant and transformation system used (Grevelding et al., 1993). Factors that regulate T-DNA copy number are poorly understood. A reproducible, broadly applicable method to increase the efficiency of producing plants with a low copy number, and preferably a single copy of the T-DNA would be highly desirable to those practicing in the art.

Recently, monocot species have been successfully transformed via Agrobacterium-mediated transformation. WO 97/48814 discloses processes for producing stably transformed fertile wheat. The method describes the recovery of transgenic, wheat plants within a short period of time using a variety of explants. Agrobacterium-mediated transformation provides a viable alternative to bombardment methods and the method also allows more efficient molecular characterization of transgenic lines. The present invention is an improved Agrobacterium-mediated transformation method that relies on the control of Agrobacterium growth during the transformation process. More specifically, the present invention focuses on controlling Agrobacterium growth in the stages of Agrobacterium-mediated transformation during which T-DNA transfer can occur.

The major deficiencies in current plant transformation systems utilizing Agrobacterium-mediated methods include but are not limited to the production efficiency of the system, and transformation difficulties due to genotype or species diversity and explant limitations. WO 94/00977 describes a method for transforming monocots that depends on the use of freshly cultured immature embryos for one monocot and cultured immature embryos or callus for a different monocot. In either system, the explants must be freshly isolated, and the method is labor intensive, genotype-, and explant-limited. Other reports rely on the use of specific strains or vectors to achieve high efficiency transformation. In one report, a specific super-binary vector must be used in order to achieve high-efficiency transformation (Ishida et al., 1996).

Despite the number of transformation methods in the art, few methods have been developed that are broadly applicable to genotypes of a single crop species as well as to genotypes of other crop species. What is lacking in the art is an Agrobacterium-mediated plant transformation system that is efficient, reproducible, applicable to a number of plant systems, and a transformation system that effectively results in transformed plants with a simple integration pattern and a low copy number. The present invention provides novel culture conditions using one or more bacterial growth inhibiting agents during inoculation and co-culture of Agrobacterium with a transformable plant cell or tissue that result in increased transformation efficiencies and a low copy number of the introduced genetic component in several plant systems. The method of the present invention consistently results in desired transgenic events with a low number of inserts and reduces the need to screen hundreds of lines for identification of the optimal commercial line for breeding and introduction of improved germplasm to plant breeders, growers, and consumers. The present invention thus provides a novel improvement compared to existing Agrobacterium-mediated transformation methods.

SUMMARY OF THE INVENTION

The present invention provides novel methods for the stable and efficient transformation of plants under conditions that inhibit the growth of Agrobacterium cells during the transformation process.

In one aspect the present invention provides a novel method of transforming a plant cell or plant tissue with Agrobacterium by inoculating a transformabe cell or tissue containing at least one genetic component capable of being transferred to the plant cell or tissue in the presence of at least one growth inhibiting agent, co-culturing in the presence or absence of the growth inhibiting agent, selecting a transformed plant cell or tissue, and regenerating a transformed plant expressing the genetic component from the selected plant cells or tissues.

In one embodiment, the growth inhibiting agent comprises a compound containing a heavy metal such as silver, or an antibiotic such as carbenicillin, or a nucleic acid, or protein capable of inhibiting or suppressing the growth of Agrobacterium cells and the growth inhibiting agent is present during the inoculation step in the transformation process and not in the co-culture step.

In another embodiment, the growth inhibiting agent that is inhibitory to Agrobacterium cell growth is absent during the inoculation step, but present in the co-culture step in the transformation process.

In still another embodiment the invention relates to the presence of at least one Agrobacterium growth inhibiting agent during the inoculation process in an amount sufficient to suppress Agrobacterium growth and reduce T-DNA transfer, thus favoring low copy insertions of the introduced DNA.

Still another aspect of the present invention relates to transformed plants produced by inoculating a transformable cell or tissue containing at least of at least one genetic component capable of being transferred to the plant cell or tissue in the presence of at least one growth inhibiting agent, co-culturing in the presence or absence of the growth inhibiting agent, selecting a transformed plant cell or tissue and regenerating a transformed plant expressing the genetic component from the selected plant cells or tissues.

Yet another aspect of the present invention relates to any seeds, or progeny of the transformed plants produced by the method of the present invention.

Further objects, advantages and aspects of the present invention will become apparent from the accompanying figures and description of the invention.

DETAILED DESCRIPTION OF THE INVENTION

Figure 1:
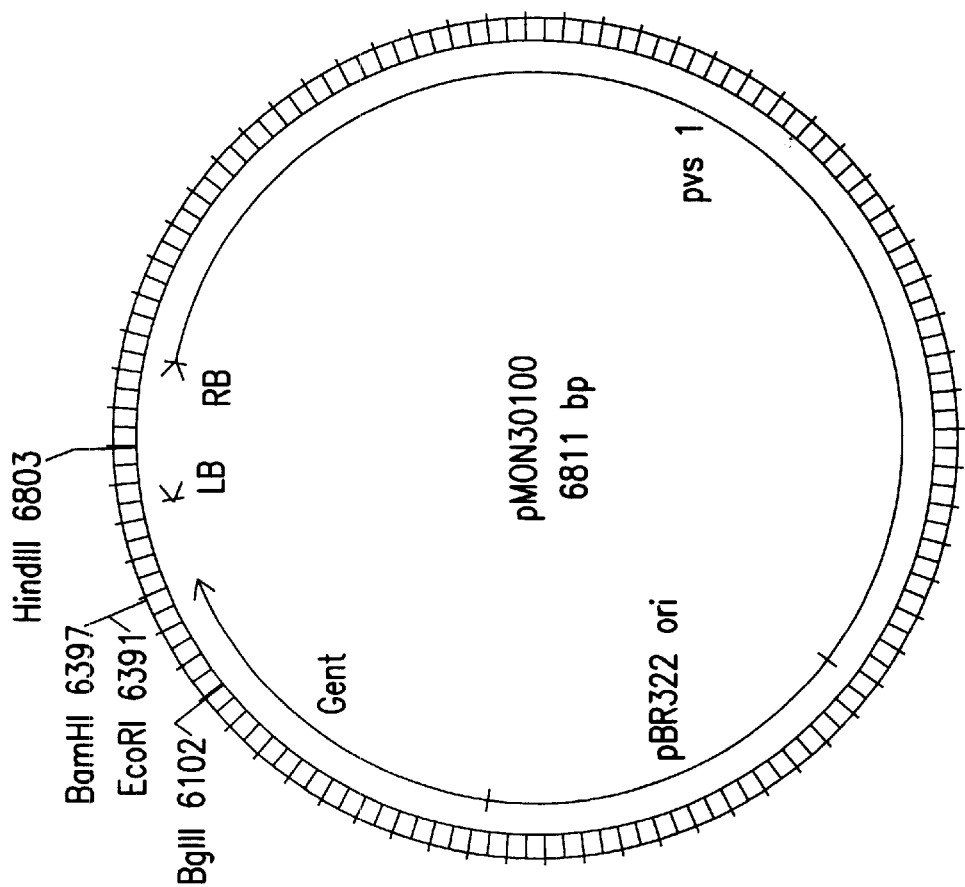
FIG. 1 is a plasmid map of pMON30100

The present invention can be used with any plant species. It is particularly useful for monocot species. Particularly preferred species for practice of the present invention include corn, wheat, and rice.

The present invention provides a transgenic plant and a method for transformation of plant cells or tissues and recovery of the transformed cells or tissues into a differentiated transformed plant. To initiate a transformation process in accordance with the present invention, it is first necessary to select genetic components to be inserted into the plant cells or tissues. Genetic components can include any nucleic acid that is introduced into a plant cell or tissue using the method according to the invention. Genetic components can include non-plant DNA, plant DNA or synthetic DNA.

In a preferred embodiment, the genetic components are incorporated into a DNA composition such as a recombinant, double-stranded plasmid or vector molecule comprising at least one or more of following types of genetic components:

(a) a promoter that functions in plant cells to cause the production of an RNA sequence, (b) a structural DNA sequence that causes the production of an RNA sequence that encodes a product of agronomic utility, and (c) a 3' non-translated DNA sequence that functions in plant cells to cause the addition of polyadenylated nucleotides to the 3' end of the RNA sequence.

The vector may contain a number of genetic components to facilitate. transformation of the plant cell or tissue and regulate expression of the desired gene(s). In one preferred embodiment, the genetic components are oriented so as to express a mRNA, that in one embodiment can be translated into a protein. The expression of a plant structural coding sequence (a gene, cDNA, synthetic DNA, or other DNA) that exists in double-stranded form involves transcription of messenger RNA (mRNA) from one strand of the DNA by RNA polymerase enzyme and subsequent processing of the mRNA primary transcript inside the nucleus. This processing involves a 3' non-translated region that adds polyadenylated nucleotides to the 3' ends of the mRNA.

Means for preparing plasmids or vectors containing the desired genetic components are well known in the art. Vectors used to transform plants and methods of making those vectors are described in U.S. Pat. Nos. 4,971,908, 4,940,835, 4,769,061 and 4,757,011, the entirety of which are incorporated herein by reference. Vectors typically consist of a number of genetic components, including but not limited to regulatory elements such as promoters, leaders, introns, and terminator sequences. Regulatory elements are also referred to as cis- or trans-regulatory elements, depending on the proximity of the element to the sequences or gene(s) they control.

Transcription of DNA into mRNA is regulated by a region of DNA usually referred to as the "promoter". The promoter region contains a sequence of bases that signals RNA polymerase to associate with the DNA, and to initiate the transcription into mRNA using one of the DNA strands as a template to make a corresponding complementary strand of RNA.

A number of promoters that are active in plant cells have been described in the literature. Such promoters would include but are not limited to the nopaline synthase (NOS) and octopine synthase (OCS) promoters that are carried on tumor-inducing plasmids of *Agrobacterium tumefaciens*, the caulimovirus promoters such as the cauliflower mosaic virus (CaMV) 19S and 35S promoters and the figwort mosaic virus (FMV) 35S promoter, the enhanced CaMV35S promoter (e35S), the light-inducible promoter from the small subunit of ribulose bisphosphate carboxylase (ssRUBISCO, a very abundant plant polypeptide). All of these promoters have been used to create various types of DNA constructs that have been expressed in plants. See, for example PCT publication WO 84/02913 (Rogers et al., Monsanto, herein incorporated by reference in its entirety).

Promoter hybrids can also be constructed to enhance transcriptional activity (Hoffman, U.S. Pat. No. 5,106,739), or to combine desired transcriptional activity, inducibility and tissue specificity or developmental specificity. Promoters that function in plants include but are not limited to promoters that are inducible, viral, synthetic, constitutive as described (Poszkowski et al., 1989; Odell et al., 1985), and temporally regulated, spatially regulated, and spatio-temporally regulated (Chau et al., 1989). Other promoters that are tissue-enhanced, tissue-specific, or developmentally regulated are also known in the art and envisioned to have utility in the practice of this invention.

Promoters may be obtained from a variety of sources such as plants and plant DNA viruses and include, but are not limited to the CaMV35S and FMV35S promoters and promoters isolated from plant genes such as ssRUBISCO genes. As described below, it is preferred that the particular promoter selected should be capable of causing sufficient expression to result in the production of an effective amount of the gene product of interest.

The promoters used in the DNA constructs (i.e. chimeric/recombinant plant genes) of the present invention may be modified, if desired, to affect their control characteristics. Promoters can be derived by means of ligation with operator regions, random or controlled mutagenesis, etc. Furthermore, the promoters may be altered to contain multiple "enhancer sequences" to assist in elevating gene expression. Examples of such enhancer sequences have been reported by Kay et al. (1987).

The mRNA produced by a DNA construct of the present invention may also contains a 5' non-translated leader sequence. This sequence can be derived from the promoter selected to express the gene, and can be specifically modified so as to increase translation of the mRNA. The 5' non-translated regions can also be obtained from viral RNAs, from suitable eukaryotic genes, or from a synthetic gene sequence (Griffiths, et al., 1993) Such "enhancer" sequences may be desirable to increase or alter the translational efficiency of the resultant mRNA. The present invention is not limited to constructs wherein the non-translated region is derived from both the 5' non-translated sequence that accompanies the promoter sequence. Rather, the non-translated leader sequence can be derived from unrelated promoters or genes. (see, for example U.S. Pat. No. 5,362,865). Other genetic components that serve to enhance expression or affect transcription or translational of a gene are also envisioned as genetic components.

The 3' non-translated region of the chimeric constructs should contain a transcriptional terminator, or an element having equivalent function, and a polyadenylation signal that functions in plants to cause the addition of polyadenylated nucleotides to the 3' end of the RNA. Examples of suitable 3' regions are (1) the 3' transcribed, non-translated regions containing the polyadenylation signal of Agrobacterium tumor-inducing (Ti) plasmid genes, such as the nopaline synthase (NOS) gene, and (2) plant genes such as the soybean storage protein genes and the small subunit of the ribulose-1,5-bisphosphate carboxylase (ssRUBISCO) gene. An example of a preferred 3' region is that from the ssRUBISCO E9 gene from pea (Fischhoff et al., European Patent Application 0385 962, herein incorporated by reference in its entirety).

Typically, DNA sequences located a few hundred base pairs downstream of the polyadenylation site serve to terminate transcription. The DNA sequences are referred to herein as transcription-termination regions. The regions are required for efficient polyadenylation of transcribed messenger RNA (mRNA) and are known as 3' non-translated regions. RNA polymerase transcribes a coding DNA sequence through a site where polyadenylation occurs.

In one preferred embodiment, the vector contains a selectable, screenable, or scoreable marker gene. These genetic components are also referred to herein as functional genetic components, as they produce a product that serves a function in the identification of a transformed plant, or a product of agronomic utility. The DNA that serves as a selection device functions in a regenerable plant tissue to produce a compound that would confer upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of transposons and associated antibiotic resistance genes include the transposons Tns (bla), Tn5 (nptII), Tn7 (dhfr), penicillins, kanamycin (and neomycin, G418, bleomycin); methotrexate (and trimethoprim); chloramphenicol; kanamycin and tetracycline.

Characteristics useful for selectable markers in plants have been outlined in a report on the use of microorganisms (Advisory Committee on Novel Foods and Processes, July 1994). These include:

i) stringent selection with minimum number of nontransformed tissues;

ii) large numbers of independent transformation events with no significant interference with the regeneration;

iii) application to a large number of species; and iv) availability of an assay to score the tissues for presence of the marker.

As mentioned, several antibiotic resistance markers satisfy these criteria, including those resistant to kanamycin (nptII), hygromycin B (aph IV) and gentamycin (aac3 and aacC4).

A number of selectable marker genes are known in the art and can be used in the present invention (see for example Wilmink and Dons, 1993). Particularly preferred selectable marker genes for use in the present invention would include genes that confer resistance to compounds such as antibiotics like kanamycin (Dekeyser et al., 1989), and herbicides like glyphosate (Della-Cioppa et al., 1987). Other selection devices can also be implemented including but not limited to tolerance to phosphinothricin, bialaphos, and positive selection mechanisms (Joersbo et al., 1998) and would still fall within the scope of the present invention.

The present invention can be used with any suitable plant transformation plasmid or vector containing a selectable or screenable marker and associated regulatory elements as described, along with one or more nucleic acids expressed in a manner sufficient to confer a particular desirable trait. Examples of suitable structural genes of agronomic interest envisioned by the present invention would include but are not limited to genes for insect or pest tolerance, herbicide tolerance, genes for quality improvements such as yield, nutritional enhancements, environmental or stress tolerances, or any desirable changes in plant physiology, growth, development, morphology or plant product(s).

Alternatively, the DNA coding sequences can effect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillitoe, 1997). Thus, any gene that produces a protein or mRNA that expresses a phenotype or morphology change of interest are useful for the practice of the present invention.

Exemplary nucleic acids that may be introduced by the methods encompassed by the present invention include for example, DNA sequences or genes from another species, or even genes or sequences that originate with or are present in the same species, but are incorporated into recipient cells by genetic engineering methods rather than classical reproduction or breeding techniques. However, the term exogenous is also intended to refer to genes that are not normally present in the cell being transformed, or perhaps simply not present in the form, structure, etc., as found in the transforming DNA segment or gene, or genes that are normally present yet that one desires, e.g., to have over-expressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

In light of this disclosure, numerous other possible selectable and/or screenable marker genes, regulatory elements, and other sequences of interest will be apparent to those of skill in the art. Therefore, the foregoing discussion is intended to be exemplary rather than exhaustive.

After the construction of the plant transformation vector or construct, said nucleic acid molecule, prepared as a DNA composition in vitro, is introduced into a suitable host such as *E. coli* and mated into another suitable host such as Agrobacterium, or directly transformed into competent Agrobacterium. These techniques are well-known to those of skill in the art and have been described for a number of plant systems including soybean, cotton, and wheat (See, for example U.S. Pat. Nos. 5,569,834, 5,159,135, and WO 97/48814 herein incorporated by reference in their entirety).

The present invention encompasses the use of bacterial strains to introduce one or more genetic components into plants. Those of skill in the art would recognize the utility of Agrobacterium-mediated transformation methods. A number of wild-type and disarmed strains of *Agrobacterium tumefaciens* and *Agrobacterium rhizogenes* harboring Ti or Ri plasmids can be used for gene transfer into plants. Preferably, the Agrobacterium hosts contain disarmed Ti and Ri plasmids that do not contain the oncogenes which cause tumorigenesis or rhizogenesis, respectfully, which are used as the vectors and contain the genes of interest that are subsequently introduced into plants. Preferred strains would include but are not limited to *Agrobacterium tumefaciens* strain C58, a nopaline-type strain that is used to mediate the transfer of DNA into a plant cell, octopine-type strains such as LBA4404 or succinamopine-type strains e.g., EHA101 or EHA105. The use of these strains for plant transformation has been reported and the methods are familiar to those of skill in the art.

The present invention can be used in any plant transformation system. Examples of suitable plant targets for the practice of the present invention would include but are not limited to alfalfa, barley, canola, corn, cotton, oats, potato, rice, rye, soybean, sugarbeet, sunflower, sorghum, and wheat. Particularly preferred dicotyledonous targets would include soybean, cotton, canola, or sunflower. Particularly preferred monocotyledonous targets would include cereals such as corn, wheat, and rice.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, callus tissue, hypocotyl tissue, cotyledons, roots, and leaves. Preferred explants for dicots include but are not limited to leaf, root, cotyledon, callus, inflorescence, hypocotyl, and stem. Preferred explants for monocots include but are not limited to immature embryos, embryogenic calli, immature inflorescence, root, shoot meristem, node, nodal explants and cell suspensions.

The explants can be from a single genotype or from a combination of genotypes. In a preferred embodiment, superior explants from plant hybrids can be used as explants. For example, a fast-growing cell line with a high culture response (higher frequency of embryogenic callus formation, growth rate, plant regeneration frequency, etc.) can be generated using hybrid embryos containing several genotypes. In a preferred embodiment an F1 hybrid or first generation offspring of cross-breeding can be used as a donor plant and crossed with another genotype. For example, Pa91 which is an inbred line is crossed with a second inbred line such as H99 and the resulting F1 hybrid plant is crossed with inbred A188. Those of skill in the art are aware that heterosis also referred to herein as "hybrid vigor" occurs when two inbreds are crossed.

The present invention thus encompasses the use of an explant resulting from a three-way or "triple hybrid" cross, wherein at least one or more of the inbreds is highly regenerable and transformable, and the transformation and regeneration frequency of the triple hybrid explant exceeds the frequencies of the inbreds individually. Other tissues are also envisioned to have utility in the practice of the present invention.

In a preferred embodiment of the present invention, immature embryos (IEs) of corn, rice, and wheat are used as explants for Agrobacterium-mediated transformation. In wheat for example, immature embryos may be isolated from wheat spikelets. The isolation of wheat immature embryos is also described by Weeks et al., (1993) and Vasil et al., (1993). Similarly, corn ears are harvested approximately 8–16 days after pollination and used as a source of immature embryos. In rice, immature caryopses are collected from plants after anthesis and immature embryos isolated from these caryopses are used as explants. The present invention thus encompasses the use of freshly isolated embryos as described. In another embodiment a suspension cell culture can be used as suitable plant material for transformation. In another embodiment a precultured tissue is used as the target plant material for transformation. By precultured as used herein is meant culturing the cells or tissues in an appropriate medium to support plant tissue growth prior to inoculation with Agrobacterium. The preculture of the transformable cells or tissue prior to Agrobacterium inoculation can occur for any length of time, for example from one day to seven days. Preferably the preculture period is less than seven days. More preferably the preculture period is three days or less. Even more preferably, the preculture of the transformable cells or tissues is from 18–28 hours.

Any suitable plant culture medium can be used for the preculture. Examples of suitable media for preculture would include but are not limited to MS-based media (Murashige and Skoog, 1962) or N6-based media (Chu et al., 1975) supplemented with additional plant growth regulators including but not limited to auxins such as picloram (4-amino-3,5,6-trichloropicolinic acid), 2,4-D (2,4-dichlorophenoxyacetic acid) and dicamba (3,6-dichloroanisic acid), cytokinins such as BAP (6-benzylaminopurine) and kinetin, and gibberellins. Other media additives can include but are not limited to amino acids, macroelements, iron, microelements, vitamins and organics, carbohydrates, undefined media components such as casein hydrolysates, an appropriate gelling agent such as a form of agar, such as a low melting point agarose or Gelrite if desired. Those of skill in the art.are familiar with the variety of tissue culture media, which when supplemented appropriately, support plant tissue growth and development and are suitable for plant transformation and regeneration. These tissue culture media can either be purchased as a commercial preparation, or custom prepared and modified. Examples of such media would include but are not limited to Murashige and Skoog (Murashige and Skoog, 1962), N6 (Chu et al., 1975), Linsmaier and Skoog (Linsmaier and Skoog, 1965), Uchimiya and Murashige (Uchimiya and Murashige, 1974), Gamborg's media (Gamborg et al., 1968), D medium (Duncan et al., 1985), McCown's Woody plant media (McCown and Loyd, 1981), Nitsch and Nitsch (Nitsch and Nitsch, 1969), and Schenk and Hildebrandt (Schenk and Hildebrandt, 1972) or derivations of these media supplemented accordingly. Those of skill in the art are aware that media and media supplements such as nutrients and growth regulators for use in transformation and regeneration and other culture conditions such as light intensity during incubation, pH, and incubation temperatures that can be optimized for the particular target crop of interest.

Once the transformable plant tissue is isolated, the next step of the method is introducing the genetic components into the plant tissue. This process is also referred to herein as "transformation." The plant cells are transformed and each independently transformed plant cell is selected. The independent transformants are referred to as transgenic events. A number of methods have been reported and can be used to insert genetic components into transformable plant tissue.

Methods for transforming dicots, primarily by use of *Agrobacterium tumefaciens*, and obtaining transgenic plants have been published for a number of crops including cotton (U.S. Pat. No. 5,064,863; U.S. Pat. No. 5,159,135; U.S. Pat. No. 5,518,908, WO 97/43430), soybean (U.S. Pat. No. 5,569,834; U.S. Pat. No. 5,416,011; McCabe et al. (1988); Christou et al. (1988), Brassica (U.S. Pat. No. 5,463,174), peanut (Cheng et al. (1996); De Kathen and Jacobsen (1990)).

Transformation of monocots using electroporation, particle bombardment, and Agrobacterium have also been reported. Transformation and plant regeneration have been achieved in asparagus (Bytebier et al. (1987)), barley (Wan and Lemaux (1994), Tingay et al., (1997)' maize (Rhodes et al. (1988); Ishida et al. (1996); Gordon-Kamm et al. (1990); Fromm et al. (1990); Koziel et al. (1993); Armstrong et al. (1995), oat (Somers et al. (1992)), rice (Toriyama et al. (1988); Zhang and Wu (1988); Zhang et al. (1988); Battraw and Hall (1990); Christou et al. (1991); Hiei et al., 1994; Park et al. (1996)), sugarcane (Bower and Birch (1992), Arencibia et al., 1998, tall fescue (Wang et al. (1992)), and wheat (Vasil et al. (1992); Weeks et al. (1993), Cheng et al., 1997)).

The present invention utilizes Agrobacterium-mediated transformation. One advantage of the present invention is that the presence of additional virulence genes is not required. Transformation was achieved in all plant systems tested. The fact that a super binary vector may not be necessary provides added utility, whereas it has been shown to be essential for achieving high transformation in another reported maize system (Ishida et al., 1996).

In a preferred embodiment, a transformable tissue is inoculated with Agrobacterium in the presence of an growth inhibiting agent. By growth inhibiting agent as used herein is meant any agent that is capable of stressing, suppressing, limiting, or inhibiting bacterial cell growth. Preferably, the growth inhibiting agent inhibits Agrobacterium cell growth. More preferably the growth inhibiting agent inhibits *Agrobacterium tumefaciens* cell growth and reduces the T-DNA transfer process. The agents referred to herein may be chemical or biological agents. Any number of methods or agents to suppress or inhibit Agrobacterium growth are envisioned. An agent that is toxic (bacteriostatic or bacteriocidal) to the Agrobacterium and less toxic to the plant cells can be included in the stages in the transformation process up to the selection step. Preferably one or more growth inhibiting agents are included with Agrobacterium at a concentration that is effective in stressing, suppressing, or inhibiting Agrobacterium growth yet remaining neutral or positive with respect to plant cell growth. Accordingly, depending on the plant system and media components, the effective concentration and duration of inclusion of the growth inhibiting agent(s) can vary and can be optimized. For example, any agent can be tested for the effect of said agent on Agrobacterium cell growth by any number of methods including but not limited to testing the agent in different concentrations, in different culture conditions, and in different plant systems using methods known to those of skill in the art. These stages for including one or more growth inhibiting agents would include any stage in a transformation process during which Agrobacterium and a plant cell are together and during which T-DNA transfer can occur. The particularly preferred transformation stages would include inoculation, wounding, and co-culture steps, including prolonged co-culture during in planta transformation methods (Bechtold et al., 1993; Clough and Bent, 1998). T-DNA transfer is a biological process and inclusion of such an growth inhibiting agent during the inoculation, wounding, co-cultivation, and/or infiltration steps can also inhibit the T-DNA processing and transfer., The growth inhibiting agent can be present either singly or in combination with other growth inhibiting agents. Examples of suitable growth inhibiting agents include but are not limited to antibiotics such as amphotericinB, carbenicillin, cefotaxime, chloramphenicol, cycloheximide, erythromycin, gentamicin A, sulphate, geneticin, hygromycin B, hydroxyquinoline, kanamycin, methotrexate, naladixic acid, neomycin sulphate, nystatin, paromomycin, penicillin, pentachloronitrobenzene, rifampicin, streptomycin, sulphonamide, tetracycline, trimethoprim, thiabendazole, ticarcillin, vancomycin, spectinomycin, compounds containing heavy metals such as silver nitrate silver thiosulfate, silver nitrite, silver di-thionate, silver stearate, silver selenate, silver salicylate, silver oxalate, silver phosphate, silyer metaphosphate, silver orthophosphate, silver orthophosphate mono-H, silver carbonate, silver propionate, silver acetate, silver citrate, silver laurate, silver levunilate, silver pyrophosphate or other silver-containing compounds, other chemicals such as compounds containing potassium, manganese, or cadmium, proteins, nucleotides, and cell extracts, cell exudates, secondary metabolites, sulfa-drugs, and growth regulators. A derivative as used herein refers to other forms of the growth inhibiting agent including but not limited to a salt derivative, an anhydrous derivative, or a hydrated derivative that are capable of inhibiting Agrobacterium growth.

Particularly preferred growth inhibiting agents would include silver nitrate, silver thiosulfate, and penicillins such as carbenicillin, ampicillin, and cloxacillin, cephalosporins such as cefotaxime and cefoxitin, or a combination antibiotic such as a penicillin plus clavulanic acid such as augmentin and timentin. The growth inhibiting agents can be "included" during the inoculation and post-inoculation stages by a number of ways, depending on the nature of the agent. Chemical agents for example can be included in the culture media by addition from a stock solution, or can be added in solid form. The agent may-be adhered to a support matrix such as a piece of filter paper and placed on semi-solid, a solid support, or liquid media. The agent can also be added to a vacuum infiltration medium or during the process of sonication-assisted Agrobacterium-mediated transformation (Trick et al., 1997).

In another embodiment, a nucleic acid sequence such as an intron can be included in the selectable marker gene to slow down or inhibit Agrobacterium cell growth during the co-cultivation and transformation process. It has been reported that a promoter of microbial origin e.g. 35S, NOS, etc., can regulate expression of genes in Agrobacterium cells. An intron-containing antibiotic marker gene can be used to inhibit Agrobacterium cells by using a differential selection strategy, e.g. nptII (conferring resistance to kanamycin), aphIV (conferring resistance to hygromycin B), acC3 and aacC4(conferring resistance to gentamycin) or aadA (conferring resistance to spectinomycin and streptomycin). For example, plant cells are rarely sensitive to kanamycin at a concentration of 25 mg/L but the same concentration is lethal to Agrobacterium cells.

In another embodiment a growth inhibiting agent is a nucleotide sequence that inhibits Agrobacterium cell growth and inhibits T-DNA processing, transfer, and integration. This can be achieved by introducing and regulating the expression of a sense or antisense gene(s) in the Agrobacterium cells. Selective regulation of such a gene or genes(s) can allow the manipulation of T-DNA mediated gene delivery.

Suitable genes would include but are not limited to metabolic genes involved in pathways for carbohydrate metabolism.

The growth inhibiting agent can be added in an amount sufficient to achieve a desired effect on Agrobacterium growth. The effective range of the agent can be manipulated to determine the optimal concentration of agent. The concentration of the growth inhibiting agent can vary depending on culture conditions including but not limited to media components and the plant system used. For example, different media components can interact with the inhibiting agent(s) and affect the amount of agent needed under certain culture conditions for a particular plant tissue system. In one embodiment, one or more growth suppressing agents can be combined and included either together, or in different stages of the transformation process. Preferably the presence of the agent(s) with Agrobacterium is effective such that the density of the Agrobacterium does not increase in the presence of the agent. More preferably, the presence of the agent(s) has a negative effect on Agrobacterium growth and has a neutral or positive effect on plant growth.

In further embodiments of the invention, the growth inhibiting agent may be included only in the inoculation step, only in the co-culture step, or in both the inoculation and co-culture steps.

Those of skill in the art are aware of the typical steps in the plant transformation process. The Agrobacterium can be prepared either by inoculating a liquid such as Luria Burtani (LB) media directly from a glycerol or streaking the Agrobacterium onto a solidified media from a glycerol, allowing the bacteria to grow under the appropriate selective conditions, generally from about 26° C.–30° C., more preferably about 28° C., and taking a single colony from the plate and inoculating a liquid culture medium containing the selective agents. Alternatively a loopful or slurry of Agrobacterium can be taken from the plate and resuspended in liquid and used for inoculation. Those of skill in the art are familiar with procedures for growth and suitable culture conditions for Agrobacterium as well as subsequent inoculation procedures. The density of the Agrobacterium culture used for inoculation and the ratio of Agrobacterium cells to explant can vary from one system to the next, and therefore optimization of these parameters for any transformation method is expected.

Typically, an Agrobacterium culture is inoculated from a streaked plate or glycerol stock and is grown overnight and the bacterial cells are washed and resuspended in a culture medium suitable for inoculation of the explant. Suitable inoculation media for the present invention include, but are not limited ½ MS PL or ½ MS VI (TABLE 3). Preferably, the inoculation media is supplemented with the growth inhibition agent. The range and concentration of the growth inhibition agent can vary and depends of the agent and plant system. For the present invention silver nitrate, silver thiosulfate, or carbenicillin are the preferred growth inhibition agents. The growth inhibiting agent is added in the amount necessary to achieve the desired effect. Silver nitrate is preferably used in the inoculation media at a concentration of about 1 $\mu$M (micromolar) to 1 mM (millimolar), more preferably 5 $\mu$M–100 $\mu$M. the concentration of carbenicillin used in the inoculation media is about 5 mg/L to 100 mg/L, more preferably about 50 mg/L. An Agrobacterium virulence inducer such as acetosyringone can also be added to the inoculation media.

In a preferred embodiment, the Agrobacterium used for inoculation are pre-induced in a medium such as a buffered media with appropriate salts containing acetosyringone, a carbohydrate, and selective antibiotics. In a preferred embodiment, the Agrobacterium cultures used for transformation are pre-induced by culturing at about 28° C. in AB-glucose minimal medium (Chilton et al., 1974; Lichtenstein and Draper, 1986) supplemented with acetosyringone at about 200 $\mu$M and glucose at about 2%. The concentration of selective antibiotics for the Agrobacterium in the pre-induction medium is about half the concentation normally used selection. The density of the Agrobacterium cells used is about $10^7$–$10^{10}$ cfu/ml of Agrobacterium. More preferably, the density of Agrobacterium cells used is about $5\times10^8$–$4\times10^9$. Prior to inoculation the Agrobacterium can be washed in a suitable media such as ½ MS.

The next stage of the transformation process is the inoculation. In this stage the explants and Agrobacterium cell suspensions are mixed together. The mixture of Agrobacterium and explant(s) can also occur prior to or after a wounding step. By wounding as used herein is meant any method to disrupt the plant cells thereby allowing the Agrobacterium to interact with the plant cells. Those of skill in the art are aware of the numerous methods for wounding. These methods would include but are not limited to particle bombardment of plant tissues, sonicating, vacuum infiltrating, shearing, piercing, poking, cutting, or tearing plant tissues with a scalpel, needle or other device. The duration and condition of the inoculation and Agrobacterium cell density will vary depending on the plant transformation system. The inoculation is generally performed at a temperature of about 15° C.–30° C., preferably 23° C.–28° C. from less than one minute to about 3 hours. The inoculation can also be done using a vacuum infiltration system.

Any Agrobacterium growth inhibiting agent or combination of agents can be included in the inoculation medium. For the present invention examples of growth inhibiting agents such as silver nitrate, silver thiosulfate, or carbenicillin are included in an MS-based inoculation medium. The concentration of silver nitrate or silver thiosulfate in the inoculation media can range from 1 $\mu$M to 1 mM, more preferably from 5 $\mu$M to 100 $\mu$M, even more preferably, from about 10 $\mu$M to 50 $\mu$M, most preferably about 20 $\mu$M. The concentration of carbenicillin the inoculation medium is from about 5 mg/L to 1000 mg/L, more preferably, about 10 mg/L to 50 mg/L, even more preferably, about 50 mg/L.

After inoculation any excess Agrobacterium suspension can be removed and the Agrobacterium and target plant material are co-cultured. The co-culture refers to the time post-inoculation and prior to transfer to a delay or selection medium. Any number of plant tissue culture media can be used for the co-culture step. For the present invention a reduced salt media such as ½ MS-based co-culture media (TABLE 4) is used and the media lacks complex media additives including but not limited to undefined additives such as casein hydolysate, and B5 vitamins and organic additives. Plant tissues after inoculation with Agrobacterium can be cultured in a liquid media. More preferably, plant tissues after inoculation with Agrobacterium are cultured on a semi-solid culture medium solidified with a gelling agent such as agarose, more preferably a low EEO agarose. The co-culture duration is from about one hour to 72 hours, preferably less than 36 hours, more preferably about 6 hours to 35 hours. The co-culture media can contain one or more Agrobacterium growth inhibiting agent(s) or combination of growth inhibiting agents. Preferably the co-culture media contains an Agrobacterium growth inhibiting agent such as silver nitrate, silver thiosulfate, or carbenicillin. The concentration of silver nitrate or silver thiosulfate is preferably about 1 $\mu$M to 1 mM, more preferably about 5 $\mu$M to 100 $\mu$M, even more preferably about 10 $\mu$M to 50 $\mu$M, most preferably about 20 $\mu$M. The concentration of carbenicillin in the co-culture medium is preferably about 5 mg/L to 100 mg/L more preferably 10 mg/L to 50 mg/L, even more preferably, about 50 mg/L. The co-culture is typically performed for about one to three days more preferably for less than 24 hours at a temperature of about 18° C.–30° C., more preferably about 23° C.–25° C. The co-culture can be performed in the light or in light-limiting conditions. Preferably, the co-culture is performed in light-limiting conditions. By light-limiting conditions as used herein is meant any conditions which limit light during the co-culture period including but not limited to covering a culture dish containing plant/Agrobacterium mixture with a cloth, foil, or placing the culture dishes in a black bag, or placing the cultured cells in a dark room. Lighting conditions can be optimized for each plant system as is known to those of skill in the art.

After co-culture with Agrobacterium, the explants can be placed directly onto selective media. The explants can be sub-cultured onto selective media in successive steps or stages. For example, the first selective media can contain a low amount of selective agent, and the next sub-culture can contain a higher concentration of selective agent or vice versa. The explants can also be placed directly on a fixed concentration of selective agent. Alternatively, after co-culture with Agrobacterium, the explants can be placed on media without the selective agent. Those of skill in the art are aware of the numerous modifications in selective regimes, media, and growth conditions that can be varied depending on the plant system and the selective agent. In the preferred embodiment, after incubation on non-selective media containing the antibiotics to inhibit Agrobacterium growth without selective agents, the explants are cultured on selective growth media. Typical selective agents include but are not limited to antibiotics such as geneticin (G418), kanamycin, paromomycin or other chemicals such as glyphosate. Additional appropriate media components can be added to the selection or delay medium to inhibit Agrobacterium growth. Such media components can include, but are not limited to antibiotics such as carbenicillin or cefotaxime.

After the co-culture step to inhibit Agrobacterium growth, and preferably before the explants are placed on selective or delay media, they can be analyzed for efficiency of DNA delivery by a transient assay that can be used to detect the presence of one or more gene(s) contained on the transformation vector, including, but not limited to a screenable marker gene such as the gene that codes for β-glucuronidase (GUS). The total number of blue spots (indicating GUS expression) for a selected number of explants is used as a positive correlation of DNA transfer efficiency. The efficiency of T-DNA delivery and the effect of Agrobacterium growth inhibiting agents on T-DNA delivery and a prediction of transformation efficiencies can be tested in transient analyses as described. A reduction in the T-DNA transfer process can result in a decrease in copy number and complexity of integration as complex integration patterns can originate from co-integration of separate T-DNAs (DeNeve et al., 1997). The effect of Agrobacterium growth inhibiting agents on reducing copy number by influencing T-DNA transfer and transformation efficiency can be tested by transient analyses and more preferably in stably transformed plants. Any number of methods are suitable for plant analyses including but not limited to histochemical assays, biological assays, and molecular analyses.

In a preferred embodiment additional experiments can be performed to assess the effect of growth inhibiting agents on Agrobacterium cells and plant growth for any plant transformation system. For example, Agrobacterium growth can be monitored in the presence and absence of one or more growth inhibiting agents at different concentrations and at different timepoints in the transformation process. In one embodiment, the effect of a growth inhibiting agent on Agrobacterium can be monitored by quantitating the recovery of Agrobacterium after a step in the process in a comparison with and without the growth inhibiting agent(s).

In another embodiment, plant cells can be infected with a wild-type tumor-inducing Agrobacterium strain and the effect of one or more growth inhibiting agents on tumor formation can be assessed by evaluating tumor formation in the presence or absence of the agent(s). T-DNA transfer can be monitored on the basis of a transient assay including but not limited to an assay for β-glucuronidase (GUS) assay (Jefferson, R. A., 1987).

The cultures are subsequently transferred to a media suitable for the recovery of transformed plantlets. Those of skill in the art are aware of the number of methods to recover transformed plants. A variety of media and transfer requirements can be implemented and optimized for each plant system for plant transformation and recovery of transgenic plants. Consequently, such media and culture conditions disclosed in the present invention can be modified or substituted with nutritionally equivalent components, or similar processes for selection and recovery of transgenic events, and still fall within the scope of the present invention.

The transformants produced are subsequently analyzed to determine the presence or absence of a particular nucleic acid of interest contained on the transformation vector. Molecular analyses can include but is not limited to Southern blots (Southern, 1975), or PCR (polymerase chain reaction) analyses, immunodiagnostic approaches, and field to evaluations. These and other well known methods can be performed to confirm the stability of the transformed plants produced by the methods disclosed. These methods are well known to those of skill in the art and have been reported (See for example, Sambrook et. al., *Molecular Cloning, A Laboratory Manual*, 1989).

Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art, should, in light of the present disclosure, appreciate that many changes can be made in the specific embodiments that are disclosed and still obtain a like or similar result without departing from the spirit and scope of the invention.

EXAMPLES

Example 1

Bacterial Strains and Plasmids

The Agrobacterium strains and binary plasmid vectors used are listed in Table 1. Plasmid vectors were constructed using standard molecular biological techniques known to one of ordinary skill in the art. Briefly, the plant transformation vectors described herein comprise one or more nucleic acid sequences including but not limited to one or more T-DNA border sequences (right border, RB; left border, LB) to promote the transfer of nucleic acid molecules into the plant genome, replication elements, a selectable marker and one or more gene(s) of interest. The plasmid vectors tested are shown in FIG. 1–FIG. 5).

A brief description of the plasmids is as follows, the e35S promoter is a modification of the 35S promoter derived from the 35S RNA of cauliflower mosaic virus (CaMV) that contains a duplication of the −90 to −300 region; the nos promoter is from *Agrobacterium tumefaciens* pTiT37. The GUS gene is the β-glucuronidase coding sequence from *E. coli* modified to have a Nco site at the start codon; ST-LS1*NT is the intron from *Solanum tuberosum*; the nptII gene (kan) codes for neomycin phosphotransferase; the nos 3' region contains downstream untranslated sequence and the poly A signal for the NOS gene of Agrobacterium tumefaciens pTiT37; ori-V is the vegetative origin of replication; ori-322 is the minimum known sequence for a function origin of replication; the CP4 gene is the coding sequence for EPSP synthase, (confers tolerance to the glyphosate herbicide); GFP is a modified coding sequence for green fluorescent protein, The selectable (nptII) and reporter genes (uidA) are driven by an enhanced 35S promoter (E35S; fig.) followed by an untranslated hsp 70 intron (Rochester et al., 1986); The uidA has an additional intron within the coding sequence to minimize bacterial expression (Vancannyet et al., 1990); the bar gene confers resistance to the herbicide bialaphos; the gent gene confers resistance to gentamycin; P-ract1 and ract1 intron refer to the rice actin promoter and rice actin intron respectively.

Binary plasmids were introduced into different Agrobacterium strains through electroporation using Bio-Rad Gene Pulser, operated at 2.5 kv and 400 Ohms. Transconjugants were selected on semi-solid Luria-Bertani medium, LB using appropriate antibiotics.

TABLE 1

Agrobacterium strains and plasmids

Figure 2:
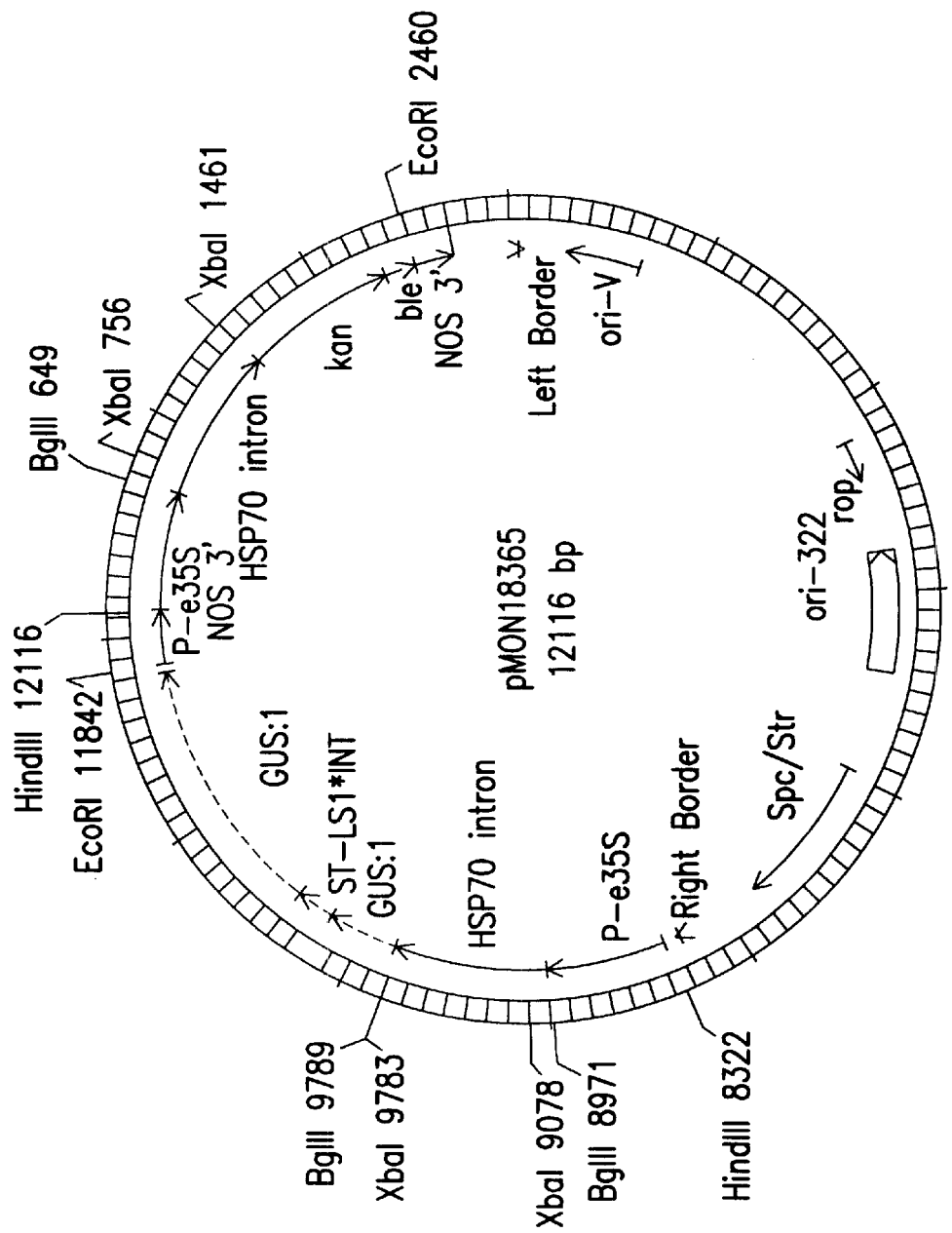
FIG. 2 is a plasmid map of pMON18365
Figure 3:
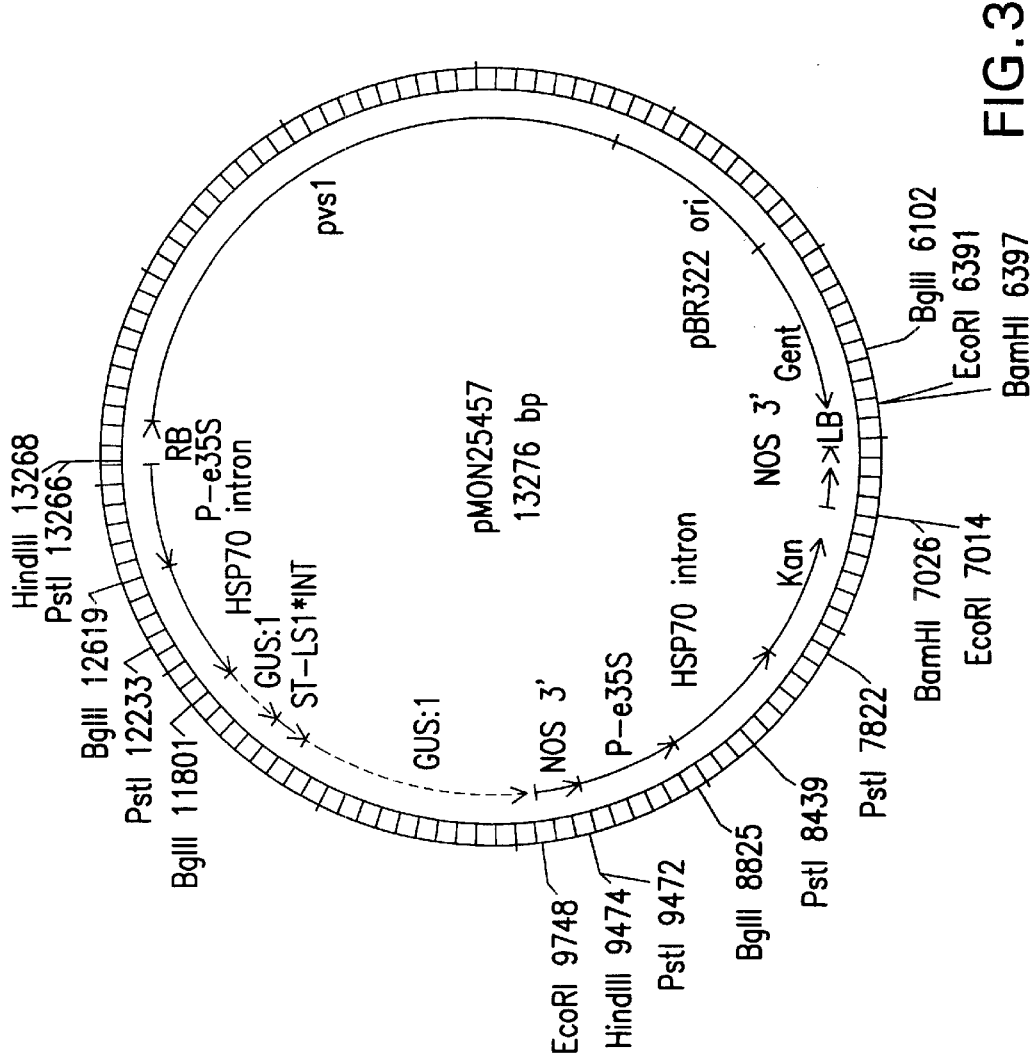
FIG. 3 is a plasmid map of pMON25457
Figure 4:
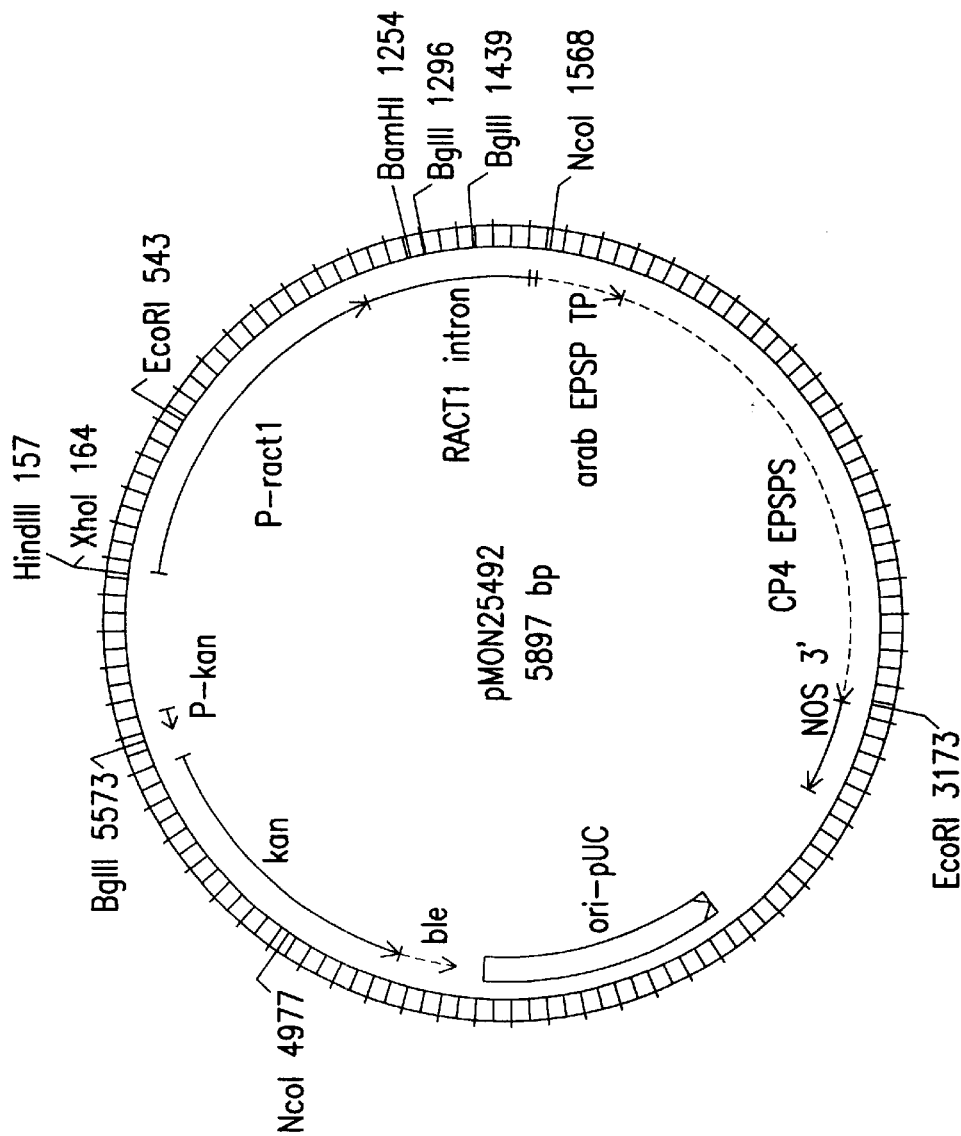
FIG. 4 is a plasmid map of pMON25492
Figure 5:
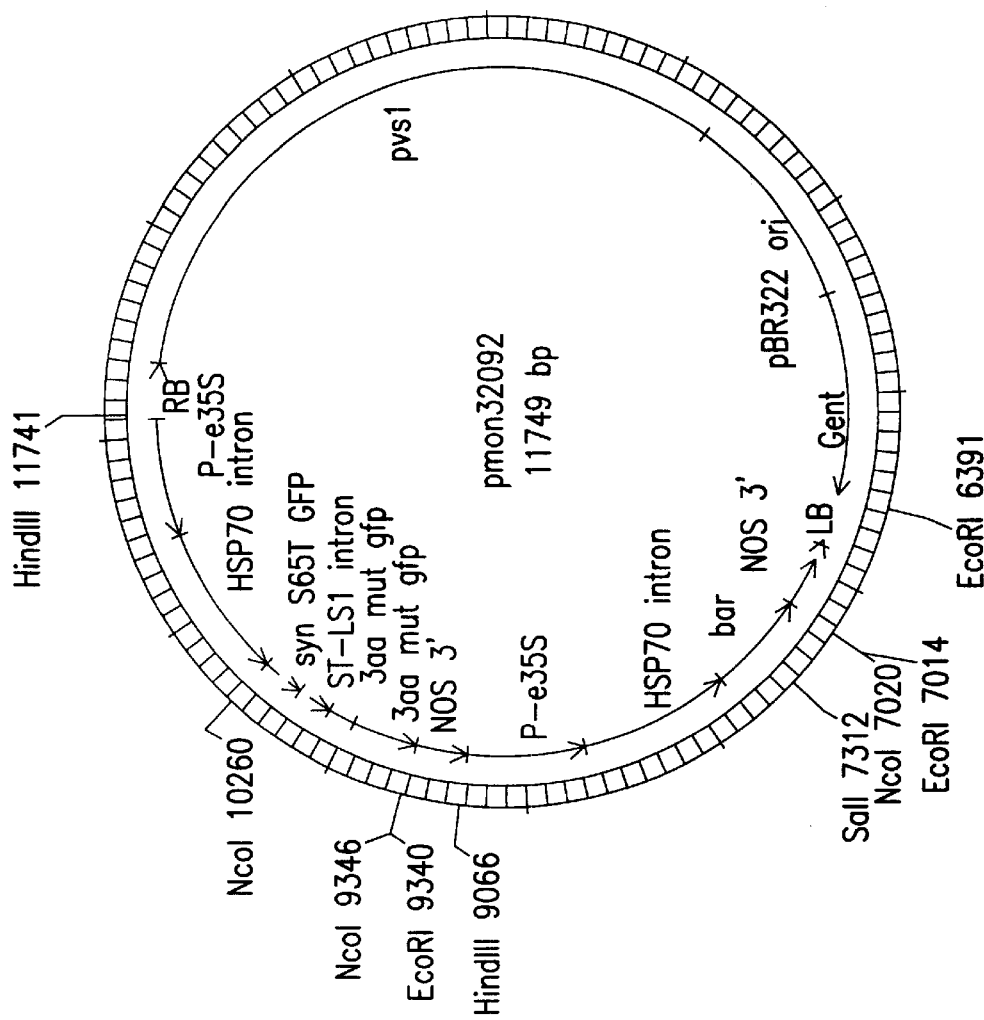
FIG. 5 is a plasmid map of pMON32092

| Strain or plasmid | Relevant characteristics | Reference/FIG. |
|---|---|---|
| A136 | C58 cured of pTiC58 | Watson et. al. 1975 |
| ABI | C58 with pMP90RK | Koncz et al. 1986 |
| A281 | A136 (pTiB0542) (succinamopine-type) | Sciaky et. al. 1978 |
| EHA 101 | Disarmed A281 | Hood et al. 1986 |
| pMON 30100 | derivative of pPZP100 | Hajdukiewicz et al. 1994, FIG. 1 |
| pMON 18365 | ABI compatible binary vector | FIG. 2 |
| pMON25457 | derivative of pMON30100 | FIG. 3 |
| pMON25492 | CP4 linear vector | FIG. 4 |
| pMON32092 | derivative of pMON30100 | FIG. 5 |

Example 2

Pre-induction of Agrobacterium

Agrobacterium cultures used for transformation are pre-induced (except as otherwise indicated) by acetosyringone (200 $\mu$M) and glucose (2%) in AB based induction medium. The procedure followed was as follows:

$1^{st}$ step:

A loopful of bacterial colonies were picked from a freshly plated plate and grown at 28° C. in 50 mls of LB medium containing appropriate antibiotics for 15–24 h. The optical density of the bacterial culture at the end of the culture period was ~1.4 at $A_{660}$.

$2^{nd}$ step:

A 10 ml aliquot of these cells were transferred into a 50 mls of fresh LB with appropriate antibiotics and grown for an another period of 6–8 h (to an optical density of ~1.2).

$3^{rd}$ step:

Agrobacterium cells were centrifuged at 4° C. for 10min at 3250 g and the pellet was resuspended in the pre-induction medium to a final optical density of 0.2 at $A_{660}$ and incubated at 28° C. for 12–15 h.

$4^{th}$ step:

Prior to use for transformation, the Agrobacterium cells were centrifuged at 4° C. for 10 min at 3250 g. After decanting the supernatant, the pellet was resuspended in ½ MS wash medium (at least 100 ml of ½ MS wash medium for 1L Agrobacterium cultures was used), aliquoted into 50 ml centrifuge tubes, centrifuged cells at 4° C. for 10 min at 3250 g, removed the supernatant and stored the tubes with pellets in ice till use (the Agrobacterium cells can be stored on ice up to 4 hr).

Reagents are commercially available and can be purchased from a number of suppliers (see, for example Sigma Chemical Co., St. Louis, Mo.).

TABLE 2

Pre-induction medium*[1]

100 mM MES (pH 5.4)
1X AB salts
0.5 mM $NaH_2PO_4$
2% Glucose
acetosyringone 200 $\mu$M

*The concentration of antibiotics in the pre-induction medium are 0.5X of the concentration used in LB medium. For example, the antibiotic concentrations used for selection of EHA101(pMON25457) grown in LB were (in $\mu$g/ml) $Kan_{100}$ plus $Gent_{100}$, and in the induction medium the level used is 50 mg/L Kanamycin and 50 mg/L Gentamycin. For C58-ABI strains selection concentrations used are: 100 mg/L Kanamycin, 100 mg/L Spectinomycin, 100 mg/L Streptomycin, and 25 mg/L Chloramphenicol in the 50 mg/L Streptomycin, and 25 mg/L Chloramphenicol in the induction medium.
[1]final concentration Example 3

Explant Preparation

Several explants were used in this study:
1) Young kalanchoe plants were grown in the green house. The leaves of this plant were used for the transformation experiment.
2) A very fine suspension cell line of Zea mays L. of Black Mexican Sweet (BMS) (BMS; Sheridan, 1975; Chourey and Zurawski, 1981), with maximum of ~100 to cells/clump size and a doubling time of approximately two days was used with the experiments with BMS. BMS cells were maintained in a modified liquid Murashige and Skoog medium, MS-BMS (Table 9). Suspension culture were maintained at 28° C. in the dark on a horizontal shaker at 150 rpm and were sub-cultured at 2 day intervals by diluting 25 mls of cell suspensions with 50 mls of fresh medium.
3) Immature embryo: Immature embryos from several crops e.g. corn, rice and wheat were used.

Corn

Several genotypes of corn were used in this study including H99, (H99XPa91)A188, H99xA188, LH198 xHi-II. Ears containing immature embryos were harvested approximately 10 days after pollination and kept refrigerated at 4° C. until use (up to 5 days post-harvest). The preferred embryo size for this method of transformation is ~1.5–2.5 mm for the hybrid (Pa91xH99) A188. This size is usually achieved 10 days after pollination inside the green house. with the following growth conditions with an average temperature of 87° F., day length of 14 hours with supplemental lighting supplied by GE 1000 Watt High Pressure Sodium lamps.

Rice

A California variety M202 was used and is publicly available. Stock plants were grown in a greenhouse with an average temperature of 78° F. day/7° F. night, day length 30 14 hours with supplemental lighting supplied by GE 1000 Watt High Pressure Sodium lamps. Immature caryopses were collected from plants 7-12-d after anthesis. IEs were dissected aseptically and either used directly for transformation or pre-cultured on MS callus induction medium (MS1) before inoculation. All cultures were incubated at the temp. of 23–25° C.

Wheat

A spring wheat Triticum aestivum cv. Bobwhite was used. Stock plants were grown in an environmentally controlled chamber with 16-h photoperiod at 800 $\mu$mol m-2 s-1 provided by high-intensity discharge Sylvania lights (GTE Products Corp., Manchester, N.H.). The day and night temperatures were 18/16° C. Immature caryopses were collected from plants 14-d after anthesis. IEs were dissected aseptically and directly used for transformation or pre-cultured on MS callus induction medium before inoculation. In other cases, cultures were incubated at 23–25° C.

Other Explants

Any other explants not described in this section are described in detail under the specific EXAMPLES.

Example 4

Inoculation

The duration and condition of the inoculation and Agrobacterium cell density varied throughout the course of this invention and are described in detail in the specific EXAMPLES.

The following method of inoculation applies to all explants other than BMS suspension cells. The procedure on BMS cell suspension transformation is described in TABLE 8. The Agrobacterium suspension was resuspended to a desired optical density (OD $A_{660}$ 1.0=$10^9$ cfu/ml) with ½ MS PL medium supplemented with acetosyringone (200 μM) and other bacteriocidal chemicals (as necessary). Three mls of this Agrobacterium suspension culture was added into a 6-well plate (Coster non treated 6-well plates, Corning Inc., Acton, Mass.). IEs were isolated for 10–15 minutes directly into each well (if using freshly isolated IEs as explants) and inoculation was performed for an additional 15 minutes after the isolation period.

After the inoculation period most of the Agrobacterium suspension was gently removed using a sterile transfer pipette. Embryos were gently collected with a sterile spatula and ~50 embryos were transferred to a single co-culture plate. During co-culture the plates containing embryos were incubated at 23° C. for 1–3 days. During the transformation process, exposure of co-culture plates to light was minimized by covering the plates with foil or a dark cloth.

TABLE 3

Inoculation media
Final Concentration:

| ½ MS VI inoculation medium* | |
|---|---|
| MS salts | 2.2 g/L (Gibco) |
| 1X MS vitamins | 1 ml of 1000X stock |
| Proline | 115 mg/L |
| Glucose | 10 g/L |
| Sucrose | 20 g/L |
| Acetosyringone | 200 μM (200 μl/l of 1M stock) |
| pH 5.4 with KOH | |
| Filter sterilize | |
| Add acetosyringone 200 μM (fresh) | |
| to the medium prior to using. | |

*Used for vacuum infiltration of BMS and IEs and for washing Agrobacterium cells

| ½ MS PL inoculation medium* | |
|---|---|
| MS salt | 2.2 g/L (Gibco) |
| 1X MS vitamins | 1 mil of 1000X stock |
| Proline | 115 mg/L |
| Glucose | 36 g/L |
| Sucrose | 68.5 g/L |
| Acetosyringone | 200 μM (200 μl/l of 1M stock) |
| pH 5.2 with KOH | |
| Filter sterilize | |
| Add acetosyringone 200 μM to the | |
| medium prior to using. | |

*Used for stable transformation of all explants except for BMS unless otherwise indicated.

Example 5

Co-culture

The conditions for co-culture (time period post-inoculation and prior to transfer of explants to delay, prolonged co-culture (kalanchoe leaves) or selection medium) varied depending on the plant system. The various media used are outlined below in the following tables.

TABLE 4*[1]

| Co-culture Medium ½ MS CC | |
|---|---|
| MS salt | 2.2 g/L (Gibco) |
| 1X MS vitamins | 1 ml of 1000X stock |
| Thiamine HCl | 0.5 mg/L |
| Proline | 115 mg/L |
| Glucose | 10 g/L |
| Sucrose | 20 g/L |
| 2,4-D | 3 mg/L |
| Low EEO agarose | 5.5 g/L |
| Acetosyringone | 200 μM (200 μl/l of 1M stock) |
| Bacteriocidal additives | described in specific EXAMPLES |
| Made 2X stock, pH 5.2 with KOH, | |
| filter sterilized | |
| Added acetosyringone (200 μM) & | |
| growth inhibiting agents to the | |
| medium prior to pouring plates. | |

*Used for stable transformation of all explants of all crops except for BMS and unless otherwise indicated.
[1]Final concentration

TABLE 5

| Co-culture Medium ½ MS BMS*[1] | |
|---|---|
| MS salts | 2.2 g/L (Gibco) |
| 1X MS vitamins | 1 mil of 1000X stock |
| Thiamine HCl | 0.5 mg/L |
| Asparagine | 150 mg/L |
| L-Proline | 115 mg/L |
| Glucose | 10 g/L |
| Sucrose | 20 g/L |
| 2,4-D | 3 mg/L |
| Acetosyringone | 200 μM (200 μl/l of 1M stock) |
| pH 5.2 with KOH, filter sterilize | |
| 200 μM Acetosyringone is added to | |
| the medium (fresh). | |

*Used for stable transformation of all explants of all crops except for BMS and unless otherwise mentioned.
[1]Final concentration

Example 6

Transformation Methods for Corn, Wheat, and Rice (Various Selectable Markers)

TABLE 6

Method for Agrobacterium-Mediated Corn Transformation

1. Inoculation:
   Inoculation duration for 15 minutes–3 hours with or without vacuum.
2. Co-culture (1–3 days):
   Duration of co-culture at 23° C. on ½ MSC (Table 4).
3. Delay (3–7 days):
   Culture on D medium (Duncan et al., 1985) supplemented with 3 mg/L 2,4-D, 250–500 mg/L Cefatoxime plus 20 μM AgNO$_3$).
4. 1$^{st}$ selection (2 wks)*:
   D medium supplemented with 500 mg/L Carbenicillin plus 50 mg/L {aromomycin. At this stage coleoptiles were removed if present and sub-culturing was not necessary) ~25 embryos/plate
   *For non-hybrid embryos < 50 mg/L Paromomycin e.g. H99 25 mg/L Paromomycin for 2 weeks
5. 2$^{nd}$ selection (2–3 wks):
   15A1A (D medium) plus 375 mg/L Carbenicillin plus 100 mg/L Paromomycin. At this stage, sub-culturing was necessary. The size of transformed sectors were usually ~2 mm and a positive embryos had only few sectors. 17 embryos/plate
6. 3$^{rd}$ selection (2–3 wks):
   D medium supplemented with 250 mg/L Carbenicillin plus 200 mg/L Paromomycin: At this stage sub-culturing was necessary.

TABLE 6-continued

Method for Agrobacterium-Mediated Corn Transformation 7. 1st regeneration (5–7 d):
   Transferred resistant pieces to the regeneration medium supplemented with 3.5 mg/L BA and 100 mg/L Carbenicillin and incubated in the dark.
8. 2nd regeneration (3 weeks):
   MSOD with 100 mg/L Carbenicillin and 50 mg/L Paromomycin

TABLE 7

Supplemental Components in Basic Media Used for Corn Transformation Using nptII*

| Components | ½MS CC² | Delay¹ | Selection¹ | Reg.¹ | MSOD² |
|---|---|---|---|---|---|
| 2,4-D (mg/L) | 3.0 | — | — | — | — |
| BAP (mg/L) | — | — | — | 3.5 | — |
| Dicamba (mM) | — | 15 | 15 | — | — |
| Glucose (g/L) | 10 | 10 | 10 | 10 | 10 |
| Sucrose (g/L) | 20 | 20 | 20 | 20 | — |
| Maltose (g/L) | — | — | — | — | 20 |
| L-Asparagine (15 mg/ml stock) | — | — | — | — | 10 ml |
| Myo-Inositol (g/L) | — | — | — | — | 0.1 |
| MS mod. Vitamins (1000X)⁴ | — | — | — | — | 1 ml |
| L-Proline (mM) | 1.0 | 12 | 12 | 12 | — |
| gelling agent (g/L)³ | 5.5 (A) | 7.0 (P) | 7.0 (P) | 7.0 (P) | 5.0 (G) |
| AgNO3 ($\mu$M)** | AgNO3 amount added as indicated in Examples | | | | |
| Carbenicillin (mg/L) | — | — | 500 | 375 | 250 |
| Cefatoxime (mg/L) | — | 250/500 | — | — | — |
| pH | 5.4 | 5.8 | 5.8 | 5.8 | 5.8 |

¹Media contained basal salts and vitamins (Duncan et al., 1985)
²Media contained basal salts and vitamins) from (Murashige and Skoog)
*All media components were filter sterilized and added to the medium after autoclaving.
³Low-EEO Agarose (A) or Phytagar ™ (P) or Agargel ™ (G) all commercially available see for example Sigma Chemical, St. Louis, MO).
⁴Table 9.

TABLE 8

Protocol for Transforming Black Mexican Sweet Suspension Cells

1. Rapidly growing BMS suspension cells were sub-cultured at an interval of 2 days by taking 25 mls of cell suspensions and diluting the suspension with 50 mls of fresh medium (MS-BMS, Table 3).
2. 10 ml of cells added (=1 ml packed cell volume) into a six well culture plates (Corning Coster nontreated 6-well plates) and removed 9.5 mls of medium.
3. Added 3 mls of pre-induced Agrobacterium suspensions (Agrobacterium preparation) and gently suspended BMS cells in Agrobacterium suspension
4. Inoculated 3 hours under vacuum
5. Removed all Agrobacterium suspension
6. Added 10 mls of wash medium
7. Plated half of the suspension cells (5.5 mls) of cell suspension from each well onto a filter paper (Baxter 5.5 catalog #F2217-55, Baxter Scientific) using a buchner funnel and vacuum
8. Transferred each filter paper with cells to co-culture medium (½ BMS co-culture supplemented with 200 $\mu$M acetosyringone). Co-culture plates were prepared by placing 2 filter papers (Baxter) soaked with 3.5 mls of co-culture media in 20 x 60 mm plates. Co-culture was performed for 1–3 days at 23° C. in the dark.
9. At the end of co-culture period, the filter paper with cells were washed with 25 mls of MS-BMS liquid plus 750 mg/L Carbenicillin under gentle vacuum using a buchner funnel. Transient analyses were performed at this stage. For the recovery of stable transformants, the entire filter paper with cells was transferred to the selection medium.

TABLE 8-continued

Protocol for Transforming Black Mexican Sweet Suspension Cells

10. Each filter paper with plated cells was transferred onto 1st selection medium (MS-BMS) supplemented with 200 mg/L Kanamycin and 750 mg/L Carbenicillin supplemented with 10% conditioning medium (prepared from one day old BMS suspension culture by taking cell free supernatant). Selection plates were prepared by putting 2 filter papers (7.0 cm Baxter, Cat#F2217-70) soaked with 5 mls of 1st selection media. Plates were sealed with parafilm and the culture was performed for 5 days at 28° C.
11. Each filter paper with cells was transferred onto semi-solid MS-BMS medium containing 20 mg/L Paromomycin and 750 mg/L Carbenicillin at 2 week intervals.
12. The efficiency of transformation was scored by counting GUS positive colonies 5 weeks after co-culture.

TABLE 9

Supplemental Components in MS Modified Medium (MS-BMS) for BMS Suspension Culture and Transformation[1,2]

| Components | Amount/Liter |
|---|---|
| 2,4-D (mg/L) | 2.0 |
| Sucrose (g/L) | 20 |
| L-Asparagine (15 mg/ml stock) | 10 ml |
| Myo-Inositol (g/L) | 0.1 |
| MS Modified Vitamins (1000X)* | 1 ml |
| pH | 5.8 |

[1]All media contain basal salts (MS basal salts) from Murashige and Skoog (1962) medium
[2]MS Modified medium (MS-BMS)
*MS Modified (MS-BMS) Vitamins 1000X stock

| Ingredient | Amount/Liter |
|---|---|
| Nicotinic Acid | 650 mg |
| Pyridoxine HCl | 125 mg |
| Thiamine HCl | 125 mg |
| Ca Pantothenate | 125 mg |

TABLE 10

Protocol for Agrobacterium-Mediated Transformation of Rice with nptII using G418 Selection

| | |
|---|---|
| 0d: | Co-cultured on CC-1 |
| 1d: | End of co-culture and transferred to MS delay with 500 mg/L Carbenicillin and 20 $\mu$M AgNO3 |
| 4d: | Removed coleoptile and cultured on the same plate |
| 7d: | End of delay and transferred to NPT-1, without sub-culture |
| 15d: | End of 1st selection. Sub-cultured into small pieces and transferred to NPT-2 (pre-regeneration medium). Incubated in the dark |
| 29d: | Transferred all callus pieces (without sub-culture) to NPT-3 (regeneration medium). Incubated in the light at 23° C. Petri-dishes were placed in a clear storage container. Lighting conditions: 75–132 $\mu$Mol photons m$^{-2}$·S$^{-2}$ |
| 43d: | Transferred all green and regenerating pieces to NPT-4 (Plantcon) without excessive sub-culture, Incubate in the light (same conditions as described above) |
| 60d | Transferred to soil |

TABLE 11

Protocol for Agrobacterium-Mediated Transformation of Rice with CP4 Gene using Glyphosate Selection

| | |
|---|---|
| 0d: | Co-cultured on CC-1 |
| 1d: | At the end of co-culture ransferred to MS delay with 500 mg/L carbenicillin and 20 $\mu$M AgNO3. |
| 4d: | Removed coleoptile and cultured on the same plate |
| 7d: | End of delay transferred to Gly-1, without sub-culture. |

TABLE 11-continued

Protocol for Agrobacterium-Mediated Transformation of Rice with CP4 Gene using Glyphosate Selection

| | |
|---|---|
| 15d: | End of 1st selection. Transferred to Gly-2 without sub-culture. Incubated in the dark. |
| 22d: | End of 2nd selection. Sub-cultured into small pieces (~1 mm pieces) and transferred to Gly-3. Incubated in the dark. |
| 37d: | Transferred all callus pieces, (without sub-culture) to Gly-4 (regeneration medium). Incubated in the light at 23° C. Placed petri-dishes directly in clear container. |
| 52d: | Transferred all green and regenerating pieces Gly-5 (Plantcon) with excessive sub-culture, (growth medium/Plantcon). Incubated in light. (75–132 $\mu$Mol photons $m^{-2} \cdot S^{-2}$ |

TABLE 12

Supplemental Components in Basic Media used for Rice Transformation Using CP4 Gene

| Components | CC1 | Delay | Gly1 | Gly2 | Gly3 | Gly4 | Gly5 |
|---|---|---|---|---|---|---|---|
| 2,4-D (mg/L) | 2.0 | | 2.0 | 2.0 | 2.0 | 0.2 | — | — |
| Picloram (mg/L)² | 2.2 | | 2.2 | 2.2 | 2.2 | — | — | — |
| BAP (mg/L)² | — | — | — | — | — | — | 2.0 | — |
| Kinetin (mg/L)² | — | — | — | — | — | — | 1.0 | — |
| NAA (mg/L)² | — | — | — | — | — | — | 1.0 | — |
| Glucose (g/L) | 10 | — | — | — | — | — | — | — |
| Sucrose (g/L) | 20 | | 20 | 20 | 20 | 20 | 60 | 60 |
| Glutamine (g/L) | — | | 0.5 | 0.5 | 0.5 | — | — | — |
| Magnesium Chloride (g/L) | — | | 0.75 | 0.75 | 0.75 | — | — | — |
| Casein Hydrolysate (g/L) | — | | 0.1 | 0.1 | 0.1 | — | — | — |
| L-Proline (mg/L) | 115 | — | — | — | — | — | — | — |
| Myo-Inositol (g/L) | — | — | — | — | — | — | 0.1 | 0.1 |
| Thiamine HCl (mg/L) | 0.5 | | 1.0 | 1.0 | 1.0 | — | — | — |
| ABA (mM) | — | — | — | — | — | 0.2 | — | — |
| Gelling agent (g/L) | 5.5 (A) | | 2 (P) | 2 (P) | 2.0 (P) | 2.5 (P) | 2.5 (P) | 2.5 (P) |
| AgNO3 ($\mu$M)* | 20* | | 20* | — | — | — | — | — |
| Carbenicillin (mg/L) | — | 500 | 250 | 250 | 250 | 250 | 100 | 100 |
| Glyphosate (mM) | — | — | 2.0 | 0.5 | 0.1 | — | 0.05 mM | |
| pH | 5.4 | 5.8 | 5.8 | 5.8 | 5.8 | 4.0 | 5.8 | 5.8 |

¹All media contain basal salts (MS basal salts) and vitamins (MS vitamins) from Murashige and Skoog (1962) medium.
²Filter-sterilized and were added to the medium after autoclaving.
³Low-EEO Agarose (A) or Phytagel ™ (P).
*Amount AgNO3 added unless otherwise indicated in specific examples.

TABLE 13

Protocol for Agrobacterium-Mediated Transformation of Wheat with nptII using G418 Selection

| | |
|---|---|
| 0d: | Co-cultured on ½MSCC |
| 1d: | End of co-culture and transferred to W1 delay with 500 mg/L carbenicillin and 20 $\mu$M AgNO3 |
| 4d: | Removed coleoptile and cultured on the same plate |
| 7d: | End of delay and transferred to W2 without sub-culture |
| 15d: | End of 1st selection. Sub-cultured into small pieces and transferred to W3 (pre-regeneration medium). Incubated in the dark |
| 29d: | Transferred all regenerating callus pieces (sub-culture) to W3 (pre-regeneration medium). Incubated in light at 23° C. (75–132 $\mu$Mol photons $m^{-2} \cdot 5^{-2}$). Placed plates directly in clear container. |

TABLE 13-continued

Protocol for Agrobacterium-Mediated Transformation of Wheat with nptII using G418 Selection

| | |
|---|---|
| 43d: | Transferred all green and regenerating pieces to W4 (Plantcon) without excessive sub-culture. Incubated in the light. |
| 60d: | Further transferred all green and regenerating pieces to W4 (Plantcon) without excessive sub-culture. Incubated in the light. |
| 75d | Transferred plantlets to soil |

TABLE 14

Supplemental Components in Basic Media used for Rice Transformation Using nptII

| Components | CC1 | Delay | NPT1 | NPT2 | NPT3 | NPT4 |
|---|---|---|---|---|---|---|
| 2,4-D (mg/L) | 2.0 | 2.0 | 2.0 | 0.2 | — | — |
| Picloram (mg/L) | 2.2 | 2.2 | 2.2 | — | — | — |
| BAP (mg/L) | — | — | — | — | 2.0 | — |
| Kinetin (mg/L) | — | — | — | — | 1.0 | — |
| NAA (mg/L) | — | — | — | — | 1.0 | — |
| Glucose (g/L) | 10 | — | — | — | — | — |
| Sucrose (g/L) | 20 | 20 | 20 | 20 | 60 | 60 |
| Glutamine (g/L) | — | 0.5 | 0.5 | — | — | — |

TABLE 14-continued

Supplemental Components in Basic Media used for Rice Transformation Using nptII

| Components | CC1 | Delay | NPT1 | NPT2 | NPT3 | NPT4 |
|---|---|---|---|---|---|---|
| Magnesium Chloride (g/L) | — | 0.75 | 0.75 | — | — | — |
| Casein Hydrolysate (g/L) | — | 0.1 | 0.1 | — | — | — |
| L-Proline (mg/L) | 115 | — | — | — | — | — |
| Myo-Inositol (g/L) | — | — | — | — | 0.1 | 0.1 |
| Thiamine HCl (mg/L) | 0.5 | 1.0 | 1.0 | — | — | — |
| ABA (mM) | — | — | — | 0.2 | — | — |
| Gelling agent (g/L) | 5.5 (A) | 2 (P) | 2 (P) | 2.5 (P) | 2.5 (P) | 2.5 (P) |
| AgNO3 ($\mu$M) | 20 | 20 | — | — | — | — |
| Carbenicillin (mg/L) | — | 500 | 250 | 250 | 100 | 100 |
| G418 (mg/L) | — | — | 40 | 40 | 40 | 40 |
| pH | 5.4 | 5.8 | 5.8 | 4.0 | | |

[1]All media contained basal salts (MS basal salts) and vitamins (MS vitamins) from Murashige and Skoog (1962) medium.
[2]Filter-sterilized and were added to the medium after autoclaving.
[3]Low-EEO Agarose (A) or Phytagel ™ (P).

TABLE 15

Supplemental Components in Basic Media used for Wheat Transformation

| Components | ½MS CC | W1 | W2 | W3 | W4 |
|---|---|---|---|---|---|
| 2,4-D (mg/L) | 3.0 | 0.5 | 0.5 | 0.2 | — |
| Picloram (mg/L) | — | 2.2 | 2.2 | — | — |
| Maltose (g/L) | — | 40 | 40 | 40 | 40 |
| Glucose (g/L) | 10 | — | — | — | — |
| Sucrose (g/L) | 20 | — | — | — | — |
| Glutamine (g/L) | — | 0.5 | 0.5 | — | — |
| Magnesium Chloride (g/L) | — | 0.75 | 0.75 | — | — |
| Casein Hydrolysate (g/L) | — | 0.1 | 0.1 | — | — |
| MES (g/L)[2] | — | 1.95 | 1.95 | 1.95 | 1.95 |
| Ascorbic Acid (mg/L)[2] | — | 100 | 100 | 100 | 100 |
| L-Proline (mg/L) | 115 | — | — | — | — |
| Thiamine HCl (mg/L) | 0.5 | — | — | — | — |
| Gelling agent (g/L)[3] | 5.5 (A) | 2 (P) | 2 (P) | 2 (G) | 2 (G) |
| AgNO3 ($\mu$M) | 20 | — | — | — | — |
| Carbenicillin (mg/L) | — | 500 | 500 | 500 | 500 |
| G418 (mg/L) | — | — | 25 | 25 | 25 |
| pH | 5.4 | 5.8 | 5.8 | 5.8 | 5.8 |

[1]All media contained basal salts (MS basal salts) and vitamins (MS vitamins) from Murashige and Skoog (1962) medium.
[2]Filter-sterilized and were added to the medium after autoclaving.
[3]Low-EEO Agarose (A) or Phytagel ™ (P) or Gelrite (G).

Example 7

Efficiency of T-DNA Delivery

The number of transgenic events in each study was determined after the plants were assayed unless indicated otherwise. The transformation efficiency (number of events/number of explants e.g. immature embryos, varied from study to study and among different treatment conditions and among different genotypes.

The efficiency of T-DNA delivery to different cell types are described in more detail in the specific examples.

Example 8

Transgenic Plant Analyses

The plants were grown in a greenhouse under appropriate growth conditions as described above. The majority of plants were fully fertile. Each plant was examined by one or more of the following methods:

a) The GUS histochemical assay (Jefferson, 1987) using different parts of the plants.
b) Biological assay (leaf bleach assay). Leaf samples (a leaf punch) from approximately 2-week-old seedlings were placed in wells of 24-well cell culture clusters (Costar Corporation, Cambridge, Mass.). Each well was filled with 0.5 ml aqueous solution composed of 300 mg/L paromomycin (Sigma) and 100 mg/L Benlate (a fungicide made by Du Pont), 100 mg/L Benlate alone was used as a control. Three leaf samples from the same leaf of each plant were placed in two wells containing paromomycin plus Benlate and one well containing Benlate alone, respectively. Leaf samples from non-transformed plants were used as negative controls. The samples were vacuum-infiltrated in a dessicator using an in-house vacuum system for 5 min and then the clusters were sealed tightly with parafilm before being placed under light (140 $\mu$Mol m-2s-1). The results were determined after 60 hours. The leaf samples that were highly resistant to paromomycin remained green in most area except the cut edges (<1 mm wide), which indicated that the plants had the functional nptII gene. The leaf samples from the plants without the gene or with the non-functional gene were bleached out completely by paromomycin as the negative controls, or had only small patches of green area.
c) Southern hybridization analysis (Southern, 1975). Genomic DNA was isolated from leaf tissue of the plants following the method of Shure et al. (1983). Ten to fifteen milligrams of genomic DNA was digested with the appropriate restriction endonuclease and fractionated on a 0.8% agarose gel. The DNA was transferred to Hybond N membranes (Amersham, Arlington Heights, Ill.) according to standard procedures (Sambrook etal., 1989). The probe for corn plants transformed with pMON18365 (FIG. 2) and pMON25457 (FIG. 3) was prepared by gel purifying a ~1.5 kb fragment containing 35s-hsp fragment. Genomic DNA of corn lines was digested with EcoR1. DNA from rice lines transformed with pMON32902 was digested with XhoI and probed with a gel purified ~1.6kb fragment from pMON25492 (FIG. 4) containing the CP4gene. The probe was labeled with 32P dCTP using a random primer labeling kit (Prime-It II, Strategene, La Jolla, Calif.), to a specific activity of 2.6×109 cpm/mg. The membrane was hybridized for 14 hours at 42° C. in a solution containing 50% formamide, 5×SSC, 5×Denhardt's, 0.5% SDS and 100kg/ml tRNA. The condition of the final wash was 0.1% SSC and 0.1% SDS at 60° C. for 15 minutes.

Example 9

Effect of the Addition of Growth Inhibiting Agents During the Growth of Agrobacterium Cells on Transformation of Plant Cells Explant Preparation Two explants are used for this study:

1) Young leaves of kalanchoe plants grown in the green house and
2) rapidly growing BMS suspension cells.

Preparation of Agrobacterium Cells

Agrobacterium cells used for transformation were pre-induced as described in Table 2 For transformation of kalenchoe leaves Agrobacterium cells were washed in the MS inoculation medium without any additives (only with salts). For the transformation of BMS suspension cells, the standard protocol as described in Table 8 was followed.

Inoculation and Co-cultivation

Transformation of BMS suspension cells was performed following the protocol described in Table 8. For transforming kalanchoe leaves, a suspension of cells from Agrobacterium strain A281 was applied after performing mechanical wounding as described in White and Nester,. The Agrobacterium strain, A136 harboring a binary vector pMON25457 (FIG. 3) was used as a negative control.

Efficiency of T-DNA Delivery

The efficiency of T-DNA delivery to BMS cells was measured by transient GUS expression post co-cultivtion as well as by staining GUS positive colonies appearing on a single piece of filter 4 weeks after co-culture.

The efficiency of T-DNA delivery to kalanchoe leaves was determined by evaluating gall formation 4 weeks post-inoculation using 20 mls of Agrobacterium A281 suspension cells.

Example 10

Effects of Addition of Growth Inhibiting Agent during Pre-induction of Agrobacterium Cells Agrobacterium cells EHA 101:pMON25457 (for transforming BMS cells) and A281 (for transforming kalanchoe leaves) were pre-induced as described above in the AB medium. During pre-induction, $AgNO_3$ was added at two different levels (20 $\mu$M and 40 $\mu$M final concentration) to the pre-induction medium. The final optical density prior to the induction was adjusted to $A_{660}$ (OD 0.2). Agrobacterium cells were pre-induced for 15 hours. Measurement of the optical density (measure of growth) was taken at the end of pre-induction, just prior to transformation. Agrobacterium cells pre-induced in the absence of $AgNO_3$ were used as a control. The effect of $AgNO_3$ during the pre-induction stage on the growth and T-DNA transfer is shown in Table 16, Table 17 and Table 18. The presence of $AgNO_3$ during growth of Agrobacterium cells prior to the transformation inhibits the growth and T-DNA transfer ability of Agrobacterium cells. Plating Agrobacterium cells on semi-solid LB plates indicated that a 15 hour culture period of Agrobacterium in the presence of $AgNO_3$ was lethal to the Agrobacterium cells. Accordingly, no stable transformants were obtained when Agrobacterium cells were treated with the growth inhibiting agent $AgNO_3$. Controls produced tumors (strain A281 on kalanchoe plant tissue) and GUS positive calli (strain EHA1010:pMON25457 on BMS suspension cells)

TABLE 16

Effect of $AgNO_3$ on Growth of Agrobacterium Cells (Pre-induction)

| Treatment | OD $A_{660}$ after 15 hours growth | Results |
| --- | --- | --- |
| minus $AgNO_3$ | 0.54 | growth |
| plus 20 $\mu$M $AgNO_3$ | 0.23 | no growth |
| plus 40 $\mu$M $AgNO_3$ | 0.24 | no growth |

TABLE 17

Effect of Addition of $AgNO_3$ During Growth of Agrobacterium on T-DNA Transfer (Tumor Induction) to Kalanchoe Cells

| Treatment | tumor formation | Results |
| --- | --- | --- |
| minus $AgNO_3$ | + | T-DNA transfer |
| plus 20 $\mu$M $AgNO_3$ | − | no transfer |
| plus 40 $\mu$M $AgNO_3$ | − | no transfer |

TABLE 18

Effect of Addition of $AgNO_3$ During Growth of Agrobacterium on T-DNA Transfer to BMS cells (Pre-Induction)

| Treatment | Average # of GUS positive colonies/filter paper | Results |
| --- | --- | --- |
| minus $AgNO_3$ | 76 | T-DNA transfer |
| plus 20 $\mu$M $AgNO_3$ | 0 | no transfer |
| plus 40 $\mu$M $AgNO_3$ | 0 | no transfer |

Example 11

Effect of Presence of Growth Inhibiting Agent during the Co-culture Period on Agrobacterium Cell Growth Plant Materials Various corn explants e.g. immature embryos isolated approximately 10 days after pollination and immature embryo derived callus, both cultured on D medium (Duncan et al., 1985); callus derived from immature embryos (TypeII callus derived from Hi-II genotype) and cultured on modified N6 medium (Armstrong et al., 1991); BMS suspension cells as described previously were used in this study.

Agrobacterium Strains and Plasmids

Disarmed *Agrobacterium tumefaciens* strain C58 (ABI) harboring binary vector pMON18365 (FIG. 2) was used in this Example. The Agrobacterium strain was pre-induced as described previously.

Inoculation and Co-cultivation

Three mls of pre-induced Agrobacterium suspension ($A_{660}$ OD 1.0) was added to a 6-well tissue culture plate. After adding the explants, the plant tissues and Agrobacterium suspension cells were subjected to vacuum infiltration for three hours. After the three hour vacuum infiltration, the Agrobacterium suspension was removed and the plant tissues were placed on semi-solid medium containing 10 $\mu$M AgNO3 (final concentration). All the tissues were incubated for three days in the dark.

Effect of AgNO3 During Co-culture on Agrobacterium cell Growth

No growth of Agrobacterium cells surrounding explants was observed on co-culture medium three days post-co-culture. All explants were transferred to the medium without the growth inhibiting agent and evaluation of Agrobacterium growth was observed seven days post-transfer. Profuse growth of Agrobacterium cells was noticed surrounding the explants. Thus, addition of the growth inhibiting agent to the co-culture medium inhibited growth of some bacterial cells, but did not kill of all Agrobacterium cells under the conditions tested.

Example 12

Effect of the Presence of Growth Inhibiting Agent During Co-Culture Period on the Recovery of Agrobacterium In an another example, immature embryos were isolated as described in Example 3. Disarmed *Agrobacterium tume-* faciens strain EHA 101 harboring binary vector pMON25457 (FIG. 3) was used. The Agrobacterium strain was pre-induced as described in Example 2. Three mls of pre-induced Agrobacterium suspension ($A_{660}$ OD 4.0) was added to a 6-well tissue culture plate as described. After adding the explants to the Agrobacterium suspension cells, the inoculation was performed for 15 minutes. The Agrobacterium suspension was removed and the embryos were placed on semi-solid medium with or without AgNO3 (20 μM final concentration). All the tissues were incubated for three days in the dark. The amount of Agrobacterium present was estimated at the beginning by randomly sampling immature embryos immediately after inoculation and again at the end of the co-culture period to determine the number of attached Agrobacterium cells per immature embryo explant. The results are presented in Table 19. The results demonstrate that inclusion of $AgNO_3$ during co-culture significantly inhibited the growth of Agrobacterium.

TABLE 19

Presence of Growth Inhibiting Agent during Co-Culture Period Reduces Agrobacterium Cell Proliferation During Co-Culture

| Treatment | Average # of Agrobacterium Colonies/Explant | Results |
|---|---|---|
| 0d | $3 \times 10^5$ CFU* | |
| 3d minus 20 μM $AgNO_3$ | $2.0 \times 10^6$ CFU | 6.7 fold increase |
| 3d plus 20 μM $AgNO_3$ | $1.0 \times 10^4$ CFU | 30 fold reduction |

*CFU = colony forming units

Example 13

Pre-induction of Agrobacterium Optimizes T-DNA Delivery When Co-Cultured in the Presence of Growth Inhibiting Agents Immature embryos of corn genotype H99xA 188 and Agrobacterium strain ABI harboring binary vector pMON18365 (FIG. 2) were used. The Agrobacterium strain was pre-induced as described previously and three mls of pre-induced Agrobacterium suspension ($A_{660}$ OD 1.0, 2.0, 3.0 and 4.0) was used. After adding the explants the Agrobacterium suspension cells, the inoculation was performed for 15 minutes. The Agrobacterium suspension was removed and embryos were placed on ½ MS corn co-culture medium supplemented with 10 μM AgNO3 (final concentration). The co-culture duration was for three days in the dark. The efficiency of T-NA delivery was estimated by a transient GUS analysis three days after co-culture by incubating embryos directly in GUS staining buffer for 12–15 hours and counting the number of GUS foci per immature embryo explant (Table 20). Increasing the concentration of Agrobacterium cells had no effect on the frequency of T-DNA transfer to corn tissues when Agrobacterium cells were grown in LB medium. For the pre-induction stage treatment, T-DNA transfer as measured by transient GUS expression increased as Agrobacterium concentration increased from an $OD_{660}$ of 1.0 to 4.0.

TABLE 20

Pre-induction of Agrobacterium Optimizes T-DNA delivery When Co-Cultured in the Presence of $AgNO_3$

| Treatment $OD_{660}$ | Induction state | Average number of GUS foci/explant |
|---|---|---|
| 1.0 | Pre-induced | 7 |
| 2.0 | Pre-induced | 28 |
| 3.0 | Pre-induced | 39 |
| 4.0 | Pre-induced | 66 |
| 2.0 | Not pre-induced (grown in LB) | 2 |
| 4.0 | Not pre-induced (grown in LB) | <1 |

Example 14

Effect of Presence of Growth Inhibiting Agent During Co-Culture on T-DNA Transfer and Plant Cell Growth Immature embryos of genotype H99xA188 were isolated as described above.

The disarmed Agrobacterium strain ABI harboring binary vector pMON18365 (FIG. 2) was used. The Agrobacterium strain was pre-induced as described above and three mls of pre-induced Agrobacterium suspension ($A_{660}$ OD 4.0) was added to a 6-well tissue culture plate as described earlier. The inoculation was performed for three hours under vacuum. The Agrobacterium suspension was removed and embryos were placed on respective semi-solid medium containing various concentrations of AgNO3 (0, 10, 20, 40, 60 μM $AgNO_3$ final concentration). All the tissues were incubated for three days in the dark. The efficiency of T-DNA delivery was estimated by a transient GUS analysis performed three days after co-culture by counting the number of GUS foci per immature embryo explant (Table 21). Efficiency of culture response was determined by transferring the embryos to a delay medium (D medium, supplemented with 500 mg/L Carbenicillin) and taking observation 2 weeks post transfer. The presence of 10 μM $AgNO_3$ during co-culture had a positive effect on both the frequency of T-DNA transfer as measured by the average number of GUS foci and tissue survival. Increasing the levels of $AgNO_3$ to 20 μM decreased the amount of T-DNA transfer but increased the frequency of the embryos responding to the culture. Increasing the level of $AgNO_3$ to 6 μM was found to be inhibitory to T-DNA transfer but the higher level did not appreciably increase the culture response. The results demonstrate that the concentration of an growth inhibiting agent such as AgNO3 can be titrated to obtain the desired efficiency of T-DNA transfer.

TABLE 21

Manipulation of T-DNA Transfer with Addition of Growth Inhibiting Agent During Co-Culture

| Treatment | Average number of GUS foci/explant | % of immature embryos responding to culture |
|---|---|---|
| minus $AgNO_3$ | 46 | 29 |
| plus 10 μM $AgNO_3$ | 63 | 42 |
| plus 20 μM $AgNO_3$ | 26 | 64 |
| plus 40 μM $AgNO_3$ | 28 | 62 |
| plus 60 μM $AgNO_3$ | 12 | 60 |

Example 15

Reduction of Agrobacterium Density during Co-Culture Using a Growth Inhibiting Agent Increases the Frequency of Transformation of Corn, Rice and Wheat

Explant Preparation

The explants used in this study were immature embryos and were prepared as described previously.

Agrobacterium Transformation and Selection:

The following transformation protocols included the following parameters: use of immature embryos that were pre-cultured for less than 24 h; a bacterial inoculation density >2.0 at $OD_{660}$, a co-culture duration of from one to three days, the use of a higher concentration of auxin or different type of auxin/combination of growth regulators than that required during normal tissue culture, a delay period 3–7 d following co-culture (with out selection pressure), no sub-culture of the original explant, a step-wise increase or decrease, depending on the crop and selection scheme and a transformation duration between 9–12 weeks.

TABLE 22

Transformation Efficiency Increases with the Addition of Growth Inhibiting Agent During Co-Culture in Corn, Rice, and Wheat

| Treatment | Transformation (%) |
| --- | --- |
| corn: | |
| $OD_{660}$ 2.0 plus 20 μM $AgNO_3$ | 18 (8/45) |
| $OD_{660}$ 2.0 minus 20 μM $AgNO_3$ | 4 (2/51) |
| $OD_{660}$ 4.0 plus 20 μM $AgNO_3$ | 8 (4/52) |
| $OD_{660}$ 4.0 minus 20 μM $AgNO_3$ | 2 (1/48) |
| (co-culture duration was three days) | |
| rice: | |
| $OD_{660}$ 2.0 plus 20 mM $AgNO_3$ | 23 (5/21) |
| $OD_{660}$ 2.0 minus 20 mM $AgNO_3$ | 4 (4/111) |
| (co-culture duration was one day) | |
| wheat: | |
| $OD_{660}$ 4.0 plus 20 mM $AgNO_3$ | 4 (1/25) |
| $OD_{6660}$ 4.0 minus 20 mM $AgNO_3$ | 0 (0/22) |
| (co-culture duration was three days) | |

Example 16

Effects of Addition of Growth Inhibiting Agents to Inoculation Media

Corn genotype LH 198 X Hi-II was used. Corn immature embryos were isolated as described previously. Approximately 30 immature embryos were inoculated for each treatment with Agrobacterium strain ABI harboring plasmid pMON18365 for five minutes and placed on co-culture media for two to three days. There were 4 replicates per treatment. The four treatments included:

Treatment 1: absence of growth inhibiting agent (in both inoculation and co-culture media)

Treatment 2: absence of agent in inoculation media; presence of agent (20 μM silver nitrate) in co-culture media.

Treatment 3: presence of agent (20 μM silver nitrate) in inoculation media; absent in co-culture media Treatment 4: presence of agent (20 μM silver nitrate) in both inoculation and co-culture media Within each treatment, five immature embryos were used for transient analysis. This was repeated across all reps within each treatment. The number of GUS spots was determined on both the scutellar surface (scutellar side up) as shown in Table 23 and the number of GUS spots was determined on the axis side of the embryos as shown in Table 24. The results demonstrated that the presence of the Agrobacterium inhibitory growth agent in the inoculation medium and co-culture medium decreased the number of GUS spots compared with the presence of the agent in either inoculation or the co-culture medium or without the inhibitory agent. Thus, presence of an Agrobacterium growth inhibiting agent in the inoculation stage and during the co-culture stage can be used to decrease T-DNA transfer and copy number. The T-DNA transfer process was also influenced by the orientation of the tissue with respect to the location of the inhibitory agent, as demonstrated by the decrease in the number of GUS spots on the axis side of the tissue which is the bottom surface of the tissue (closest to the growth inhibiting agent on the co-culture plate) (Table 24)

TABLE 23

Effects of Presence or Absence of Growth Inhibiting Agent in Inoculation Media (MS-PL) and/or Co-culture Media (½MS CC) on Transient GUS Expression

| Treatment | Average # GUS spots/embryo (scutellar surface) | Duncan Grouping* |
| --- | --- | --- |
| 1 (none) | 80.4 | A |
| 2 (inoculation) | 82.5 | A |
| 3 (co-culture) | 81.8 | A |
| 4 (both) | 58.9 | A |

*Means with same letter indicate no significant difference according to Duncan's New Multiple Range Test at a 5% probability level.

TABLE 24

Effects of Presence or Absence of Growth Inhibiting Agent in Inoculation Media (MS-PL) and/or Co-culture Media (½MS CC) on Transient GUS Expression

| Treatment | Average # GUS spots/embryo (axis) | Duncan Grouping* |
| --- | --- | --- |
| 1 (none) | 39.1 | A |
| 2 (inoculation) | 40.8 | A |
| 3 (co-culture) | 3.8 | B |
| 4 (both) | 8.4 | B |

*Means with same letter indicate no significant difference according to Duncan's New Multiple Range Test at a 5% probability level.

Example 17

Addition of Growth Inhibiting Agent during Inoculation Improves Transformation Efficiency in Corn.

Immature embryos of genotype (H99xPa 91)A 188 were isolated as described. The Agrobacterium strain EHA 101 harboring binary vector pMON25457 (FIG. 3) was used. The Agrobacterium strain was pre-induced as described and three mls of pre-induced Agrobacterium suspension ($A_{660}$ OD 0.5) supplemented with 20 μM AgNO3 was added to a 6-well tissue culture plate as described above. Inoculation was performed for 15 minutes. The Agrobacterium suspension was removed and embryos were placed on semi-solid co-culture medium containing 20 μM $AgNO_3$ (final concentration). All the tissues were incubated for three days in the dark. The transformation protocol followed as described in Example 6. Control embryos were cultured in the absence of $AgNO_3$ in all steps of the transformation process. Transformation efficiency was calculated based on the number of embryos producing paromomycin resistant calli. The results demonstrate that the addition of a growth inhibition agent such as AgNO3 during inoculation increases the transformation efficiency.

TABLE 25

Inclusion of Growth Inhibiting Agent AgNO$_3$ During Inoculation Improves Transformation Efficiency in Corn*

| Treatment condition | % Transformation* |
| --- | --- |
| No AgNO$_3$ | 1.5 (1/65) |
| 5d 20 µM AgNO$_3$*[1] | 7.8 (4/51) |
| 8d 20 µM AgNO$_3$*[2] | 9.0 (5/55) |

*data in the parenthesis indicates total number of embryos producing Paromomycin positive events/total number of embryos inoculated.
*[1]AgNO$_3$ was not present during 3 day co-culture period but was present during inoctilation and 5 day delay period following co-culture.
*[2]AgNO$_3$ was present during inoculation, 3 day co-culture and 5 day delay period.

Example 18

Effects of Other Chemicals on Growth of Agrobacterium

Each of the chemicals listed in Table 26 was resuspended in MS-BMS media and added (final concentration 50 µM) to a 50 ml overnight culture of Agrobacterium (strain ABI). Twenty-four hours after inoculation the effect of the chemicals on the growth of Agrobacterium was recorded. A known bacteriocidal compound, Carbenicillin at a final concentration of 50 mg/L and AgNO3 (20 µM) were used as controls. "No Growth" indicates there was not an increase in cell density indicating bacteriocidal or bacteriostatic property of the chemical, "Slow Growth" indicates that a slight increase in cell density was noticed and a higher level may be lethal. "Growth" indicates no effect on bacterial growth at the concentration used relative to growth in control medium, and a higher concentration may be needed to elicit an effect on growth.

TABLE 26

Bacteiocidal or bacteriostatic properties of different chemicals on Agrobacterium

| Chemical | Effect |
| --- | --- |
| Aluminum Chloride | Growth |
| Cadmium Chloride | Slow Growth |
| Chromium (II) Chloride | Growth |
| Lead Nitrate | Growth |
| Manganese Chloride | Slow Growth |
| Nickel Chloride | Growth |
| Potassium Chromate | No Growth |
| Silver Nitrate | No Growth |
| Sodium Molybdate | Growth |
| Sodium Tungstate | Growth |
| Zinc Chloride | Growth |
| Carbenicillin | No Growth |

Example 19

Improvements in Transformation of Corn by Reduction of Agrobacterium Density During Co-Culture with Different Growth Inhibiting Agents Immature embryos of genotype (H99xPa 91)A 188 were isolated as described. The Agrobacterium strain EHA 101 harboring binary vector pMON25457 (FIG. 3) was used. The Agrobacterium strain was pre-induced as described. The inoculation was performed using a concentration of A$_{660}$ OD 4.0 for 15 minutes as described. Post inoculation, Agrobacterium suspension was removed and embryos were placed on different semi-solid co-culture media supplemented with various bacteriocidal compounds. All the tissues were incubated for three days in the dark. The transformation protocol followed was as described previously (corn IE transformation) except that the $1^{st}$ selection with 50 mg/L Paromomycin was replaced with 25 mg/L Paromomycin for 2 weeks and 50 mg/L Paromomycin for 2 additional weeks. Transformation efficiency was calculated based on the number of embryos producing nptII positive plants as determined by a leaf bleach assay as described earlier. Three weeks after the transformation, the quality and growth characteristics of IE-derived callus co-cultured in the presence of different growth inhibiting agents. The culture response on different co-culture media containing different agents was as follows: 50 µM AgNO3 produced embryogenically the most competent callus>20 µM AgNO3>Carbenicillin>without additives>K2CrO4 produced embryogenically less competent callus. The results demonstrate that a higher frequency of transformation can be obtained when an growth inhibiting agent such as silver nitrate is added during the co-culture period. A decreased level of transformation (reduced frequency of T-DNA transfer) was obtained when the concentration of AgNO3 was increased from 20 µM to 50 µM, although a higher culture response was achieved. Addition of K2CrO4 was detrimental, presumably due to extreme negative effects of this chemical on plant cell health in addition to the effects of the chemical on Agrobacterium. The data demonstrated that the increase in transformation effciency was related to inhibiting the Agrobacterium growth during the co-culture rather than the improvements in the culture response.

TABLE 27

Transformation Efficiency Improvements of Corn by Using Different Growth Inhibiting Agents During Co-Culture

| Treatment | % Transformation* |
| --- | --- |
| 50 µM AgNO$_3$ | 6.3 (6/95) |
| 20 µM AgNO$_3$ | 16 (9/56) |
| 50 µM K2CrO4 | 0 (0/104) |
| Carbenicillin (50 mg/L) | 14.3 (5/35) |
| no chemicals | 2.6 (2/77) |

*data in the parentheses indicate total number of embryos producing paromomycin positive events/total number of embryos inoculated.

Example 20

Novel Explants for Transforming Cereals with Agrobacterium: Improvements in Transformation of Corn by Using Hybrid Embryos Containing Three Genotypes Hybrid corn embryos were used to test the effect of an growth inhibiting agent for improving the transformation process. The data presented in the Table 28 demonstrated that the use of a faster dividing cell line can increase the frequency of transformation. Furthermore, faster cell division may allow the selection/elimination of transgenic events containing complex or multiple copies of inserts.

Immature embryos of different corn genotypes e.g. H99, H99xA188 and (H99xPa 91)A188 were isolated as described. The Agrobacterium strain EHA 101 harboring binary vector pMON25457 (FIG. 3) or ABI harboring binary vector pMON18365 (FIG. 2) were used. Agrobacterium strain was pre-induced as described the inoculation was performed using a concentration of $A_{660}$ OD 4.0 for 15 minutes as described. Post-inoculation, the Agrobacterium suspension was removed and embryos were placed on semi-solid co-culture medium supplemented with 20 μM AgNO3. All the tissues were incubated for three days in the dark. The transformation protocol followed was as described previously except that with the genotype H99 the $1^{st}$ selection with 50 mg/L paromomycin was replaced with 25 mg/L paromomycin for two weeks and 50 mg/L paromomycin for two additional weeks. Transformation efficiency was calculated based on the number of embryos producing nptII positive plants as determined by a leaf bleach assay as described earlier. It is evident from the data presented in the Table 28 that the use of a faster dividing cell line containing 3 genotypes produced a higher frequency of transformation

TABLE 28

Improvements in Transformation of Corn by Using Hybrid Embryos Explants Containing Three Genotypes and a Growth Inhibiting Agent

| Genotype | % Transformation* |
|---|---|
| H99 | 2.4 (4/164)[2] |
| H99 | 1.2 (8/683)[2] |
| H99 | 1.0 (8/745)[2] |
| H99XA188 | 1.7 (2/114)[1] |
| (H99XPa91)A188 | 4.9 (25/508)[1] |
| (H99XPa91)A188 | 12.2 (50/409)[2] |

*data in the parenthesis indicate the total number of embryos producing paromomycin positive events/total number of embryos inoculated.
[1]ABI:pMON18365
[2]EHA101:pMON25457

Example 23

Production of Transgenic Events with Lower Copy Number Inserts Using Bacteriocidal Compounds During the Co-Culture Medium.

Immature embryos of corn and rice were transformed with the Agrobacterium strain ABI 101 harboring the binary vector pMON18365 (FIG. 2) and EHA 101 harboring the binary vector pMON32092 (FIG. 5) using methods containing an growth inhibiting agent during the co-culture as described above. The analysis of copy number was performed using Southern hybridization as previously described. The data presented in the Table 29 demonstrated that the use of a growth inhibiting agent resulted in the production plants with 1–2 copy number of inserts at a very high frequency compared to what has been achieved with other transformation system published to date (Hiei et al., 1994 and Isida et al., 1996).

TABLE 29

Reduction of Agrobacterium Density During Co-Culture Increases Frequency of Stable Transformation of Corn and Rice

| | | Copy number | |
|---|---|---|---|
| Crop | Vector | % 1 insert | % 2 inserts |
| corn | ABI:pMON18365 | 83 (15/18) | 17 (3/18) |
| rice | EHA101:pMON32092 | 42 (21/50) | 42 (21/50) |

Example 22

Production of Transgenic Events with Higher Co-expression of the Reporter Gene

Immature embryos of corn and rice were transformed with the Agrobacterium strains ABI 101 harboring the binary vector pMON18365 (FIG. 2) and EHA 101 harboring the binary vector pMON25457 (FIG. 3) using methods including an growth inhibiting agent during the co-culture as described. The efficiency of co-transformation was determined by determining the number of nptII positive plants expressing GUS using histochemical staining as described. The data presented in the Table 30 demonstrated that the use of an growth inhibiting agent resulted in the production of plants with a high co-expression frequency.

TABLE 30

Production of Transgenic Events with Higher Co-Expression of the Reporter Gene

| Crop | Vector | % Co-expression |
|---|---|---|
| corn | EHA101:pMON25457 | 98 (98/107) |
| rice | EHA101:pMON25457 | 88 (30/34) |

Example 23

Production of Transgenic Events with Higher Co-Expression of the Reporter Gene

Immature embryos of corn of two different genotypes were transformed with the Agrobacterium strain EHA 101 harboring the binary vector pMON25457 (FIG. 3) using methods containing an growth inhibiting agent during the co-culture as described above. The segregation analysis were performed germinating immature embryos of corn 12–14 days post controlled pollination (back crossing) on MSOD medium containing 100 mg/L Paromomycin. The data presented in the Table 31 demonstrated that the use of an growth inhibiting agent resulted in the production of plants with higher events with the presence of transgene at a single locus. Evidence was presented earlier that the majority of this locus contain lower copy inserts (>50% single copy for rice and >87 for corn). Furthermore, it is also evident from the results that combination of 3 or more genotypes results in a higher number of plants with single segregating locus than H99, supporting our earlier results that faster cell division allowed the selection/elimination of transgenic events containing complex or multiple copies of inserts.

TABLE 31

Production of transgenic events with simple segregation pattern in corn

| | | segregating locus | |
|---|---|---|---|
| Genotype | vector | % single* | % > single* |
| (H99 × Pa91)A188 | EHA101:pMON25457 | 90 (69/77) | 10 (8/77) |
| H99 | EHA101:pMON25457 | 80 (16/20) | 20 (4/20) |

Example 24

Higher Concentration of Auxin(s) with Addition of Growth Inhibiting Agent Improves the Transformation Efficiency in Rice Immature embryos of rice were transformed with the Agrobacterium strain EHA 101 harboring the binary vector pMON25457 (FIG. 3) using methods including an growth inhibitory agent, 20 μM AgNO3 during the co-culture as described. The transformation efficiency was determined on nptII positive events/total number of embryos inoculated as previously described. The results demonstrated that the combination of auxins or using 2 mg/L of 2,4-D with the addition of picloram during co-culture improves transformation efficiency. Furthermore, the corn transformation protocol described earlier used 3 mg/L of 2,4-D in the co-culture medium, a level that is often too high for embryogenic callus induction as well as regular maintenance of embryogenic callus of corn.

TABLE 32

Higher Concentration of Auxin(s) Improves the Transformation Efficiency in IEs of Rice*

| Plasmid Vector | Co-culture medium** | % Transformation |
|---|---|---|
| EHA101:pMON25457 | CC1 | 21 (23/108) |
| (EHA101:pMON25457 | CC2 | 12 (14/118) |

*EHA101:pMON25457
**media recipe in Table 33

TABLE 33

Supplemental Components in Basic Media used During Co-culture of Rice Immature Embryos (IEs)*[1]

| Components | CC1 | CC2 |
|---|---|---|
| 2,4-D (mg/L) | 2.0 | 2.0 |
| Picloram (mg/L) | 2.2 | — |

*All other components of the media are similar to ½ MSCC.
[1]All media contain basal salts (MS Basal Salts) and vitamins (MS vitamins) from Murashige and Skoog (1962) medium.
[2]Filter-sterilized and were added to the medium after autoclaving.

REFERENCES

The references listed below and all references cited herein are incorporated herein by reference to the extent that they supplement, explain, provide a background for, or teach methodology, techniques, and/or compositions employed herein.

U.S. Pat. No. 4,757,011
U.S. Pat. No. 4,769,061
U.S. Pat. No. 4,940,835
U.S. Pat. No. 4,971,908
U.S. Pat. No. 5,064,863
U.S. Pat. No. 5,106,739
U.S. Pat. No. 5,159,135
U.S. Pat. No. 5,384,253
U.S. Pat. No. 5,416,011
U.S. Pat. No. 5,463,174
U.S. Pat. No. 5,518,908
U.S. Pat. No. 5,569,834
U.S. Pat. No. 5,631,152
Intl. Pat. Appl. Publ. No. WO 84/02913
Intl. Pat. Appl. Publ. No. WO 94/00977
Intl. Pat. Appl. Publ. No. WO 97/43430
Intl. Pat. Appl. Publ. No. WO 97/48814
Arecoboa et at., Transgenic Res. 7:213–222.
Armstrong et al., Maize Genet. Newslett. 65:92–93, 1991.
Armstrong et al., Crop Science, 35:550–557, 1995.
Battraw and Hall, Plant Sci. 86(2):191–202, 1992.
Bechtold et al., C.R. Acad. Sci, Paris, Life Sciences 316, 1194–1199.
Bower and Birch, Plant J., 5:299, 1994.
Binns and Howitz, 1994, In Bacterial Pathogenesis of Plants and Animals (Dang, J. L., ed.). Berlin: Stringer Verlag, pp. 119–138, 1994
Bird et al., Biotech Gen. Engin. Rev., 9:207–227, 1991.
Bytebier et al., Proc. Natl. Acad. Sci. USA 84:5345, 1987.
Capecchi, Cell, 22(2):479–488, 1980.
Clapp, Clin. Perinatol., 20(1):155–168, 1993.
Chau etal., Science, 244:174–181, 1989.
Chilton et al., Proc. Natl Acad. Sci. USA, 71:3672–3676.
Christou et al., Bio/Technology 9:957, 1991.
Christou et al., Plant Physiol., 87:671–674, 1988.
Cheng et al., Plant Cell Rep., 15(9):653–657, 1996.
Cheng et al., Plant Physiol. 115(3): 971–980, 1997.
Chu et al., Scientia Sinica 18:659, 1975.
Clough and Bent, Plant J. 16:735–743, 1998.
Chourey and Zurawski, Theor. Appl Genet., 59:341–344, 1981.
Curiel et al., Hum. Gen. Ther., 3(2):147–154, 1992.
Datta et al., Bio/Technology, 8:736–740, 1990.
Davey et al., J. Exp. Bot., 42:1129–1169, 1991.
Della-Cioppa et al., Bio/Technology, 5:579–584, 1987.
De Kathen and Jacobsen, Plant Cell Rep., 9(5):276–279, 1990.
Dekeyser et al., Plant Physiol., 90:217–223, 1989.
De Neve et al. Plant J. 11:15–29, 1997.
Duncan et al., Planta, 165:322–332, 1985.
Eglistis and Anderson, Biotechniques, 6(7):608–614, 1988.
Fromm et al., Proc. Natl. Acad. Sci. USA, 82(17): 5824–5828, 1985.
Fromm-et al., Bio/Technology, 8:833–839, 1990.
Fynan et al, Proc. Natl. Acad. Sci. USA, 90(24): 11478–11482, 1993.
Gamborg et al., Exp. Cell Res., 50:151, 1968.
Gelvin, In Transgenic Plants, S. D. Kung and R. Wu eds., Academic Press, San Diego, pp. 49–87, 1993.
Gibson, S. A. and E. J. Shillitoe, Mol. Biotech. 7:125–137, 1997.
Gordon-Kamm et al., Plant Cell, 2:603–618, 1990.
Graham and Van der Eb, Virology, 54(2):536–539, 1973.
Grevelding et al, 1993, Plant Mol. Biol. 23:847–860, 1993.
Hajdukiewicz et al., Plant Mol. Biol. 25: 989–994, 1994.
Hiei et al., Plant J. 6: 271–282, 1994.
Hood et al., J. Bacteriol. 168: 1283–1290, 1986.
Hooykaas and Beijersbergen, Ann. Rev. Phytopathol. 32:157–179, 1994.
Howard and Citovsky, Bioassays, 12:103–108, 1990.
Ishida, Y, et al., Nature Bioteh., 745–750, 1996.
Jefferson, Plant Mol. Biol.Rep., 5:387–405, 1987.
Joersbo et al., Mol. Breed., 4:111–117, 1998.
Jones et al., Mol. Gen. Genet. 207: 478–485, 1987.
Jorgensen et al., Mol. Gen. Genet. 207: 471–477, 1987.
Kado, Crit. Rev. Plant Sci. 10:1–32, 1991.
Kay et al., Science, 236:1299, 1987.
Koncz et al. Plant Mol. Biol Manual B2: 1–22, 1994
Koziel et al., Bio/Technology, 11:194, 1993.

Knutson et al., *Proc. Natl. Acad. Sci. USA*, 89:2624–2628, 1992.
Lessl and Lanka, *Cell* 77:321–324, 1994.
Lichtenstein and Draper, in *DNA Cloning: A Practical Approach*, ed. Glover, D. M. (IRL, Washington, D.C., vol 2:67–119, 1985.
Linsmaier and Skoog, *Physio. Plant.*, 18: 100, 1965.
Lu et al., *J. Exp. Med.*, 178(6):2089–2096, 1993.
McCabe et al., *Bio/Technology*, 6:923, 1988.
McCown, B. and G. Lloyd, *HortScience* 16:453, 1981.
Mursahige and Skoog, *Physiol. Plant*, 15:473–497, 1962.
Nitsch, J. P. and C. Nitsch, Science 163:85–87, 1969.
Odell et al., *Nature*, 313:810, 1985.
Park et al., *Plant Mol. Biol.*, 21:415–428, 1993.
Park et al., *Plant Mol. Biol.* 32(6):1135–1148, 1996.
Piorer et al., *Science*, 256:520–523, 1992.
Poszkowski et al., *EMBO J.*, 3:2719, 1989.
Ream, *Ann. Rev. Phytopathol.* 27: 583–618.
Rhodes et al., *Science*, 240:204, 1988.
Sambrook et al., *Molecular Cloning, A Laboratory Manual*, 1989.
Schenk and Hildebradnt, *Can. J. Bot.* 50:199–204, 1972.
Sciaky et al., *Plasmid* 1: 238–253, 1978.
Sheridan, *J. Cell Biol.*, 67, 396a, 1975.
Shimamoto et al., *Nature*, 338:274–276, 1989.
Shure et al., *Cell*, 35:225–233, 1983.
Somers et al., *Bio/Technology* 10:1589, 1992.
Southern, *J. Mol. Biol.*, 98:503–517, 1975.
Toriyama et al., *Theor Appl. Genet.* 205:34, 1986.
Trick et al., *Tissue Cult. Biotechnol.* 3: 9–26, 1997.
Uchimiya and Murashige, *Plant Physiol.* 15:473, 1962.
Vasil et al., *Bio/Technolgy*, 111:1 153–1158, 1993.
Wagner et al., *Proc. Natl. Acad. Sci. USA*, 89(13): 6099–6103, 1992.
Wan and Lemaux, *Plant Physiol.* 104:37, 1994.
Watson et al., *J. Bacteriol.* 123. 225–264, 1975.
Weeks et al., *Plant Physiol*, 102:1077–1084, 1993.
White and Nester, *J. Bacteriol.* 141:1134–1141, 1980.
Wilmink and Dons, *Plant Mol. Biol. Rep.* 11, 165–185, 1993.
Winnans, *Microbiol. Rev.* 56: 12–31, 1992.
Wong and Neuman, *Biochim. Biophys. Res. Commun.*, 107(2):584–587, 1982.
Vasil et al., *Bio/Technology*, 10:667–674, 1992.
Vasil et al., *Bio/Tech*, 11:1553–1558 (1993).
Wang et al., *Bio/Technology* 10:691, 1992.
Weeks et al., *Plant Physiol.*, 102:1077–1084, 1993.
Weeks et al., *Plant Physiol.*, 104:37, 1994.
Zambryski, *Annual Rev. Plant Physiol. Plant Mol. Biol.*, 43: 465–490, 1992.
Zatloukal et al., *Ann. N.Y. Acad. Sci.*, 660:136–153, 1992.
Zhang and Wu, *Theor. Appl. Genet.* 76:835, 1988.
Zhang et al., *Plant Cell Rep.*, 7:379, 1988.
Zhou et al., *Plant Cell Tissue Organ Culture*, 30:78–83, 1992.
Ziauddin et al., *Plant Cell Rep.*, 11:489–493, 1992.
Zupan and Zambryski, *Annual Rev. Phytopathol.* 27, 583–618, 1995.

What is claimed is:

1. A method of transforming a corn plant cell or plant tissue using an Agrobacterium mediated process comprising the steps of:

inoculating a transformable plant cell or tissue from a corn plant with Agrobacterium containing at least one genetic component capable of being transferred to the plant cell or tissue in an inoculation media containing an effective amount of at least one antibiotic that inhibits or suppresses the growth of Agrobacterium;

co-culturing the transformable plant cell or tissue after the inoculating step in a medium capable of supporting growth of plant cells or tissue expressing the genetic component, said medium not containing said antibiotic;

selecting transformed plant cells or tissue; and regenerating a transformed corn plant expressing the genetic component from the selected transformed plant cells or tissue.

2. The method of claim 1 wherein the antibiotic is carbenicillin.

3. The method of claim 1 wherein the transformable plant cell or tissue from corn is an immature embryo.

4. A method of transforming a plant cell or plant tissue using an Agrobacterium mediated process comprising the steps of:

inoculating a transformable plant cell or tissue from a dicotyledonous plant with Agrobacterium containing at least one genetic component capable of being transferred to the plant cell or tissue in an inoculation media containing an effective amount of at least one antibiotic that inhibits or suppresses the growth of Agrobacterium;

co-culturing the transformable plant cell or tissue after the inoculating step in a medium capable of supporting growth of plant cells or tissue expressing the genetic component, said medium not containing said antibiotic;

selecting transformed plant cells or tissue; and regenerating a transformed plant expressing the genetic component from the selected transformed plant cells or tissue.

5. The method of claim 4 wherein the dicotyledonous plant is soybean cotton canola, or sunflower.

6. The method of claim 4 wherein the antibiotic is carbenicillin.

* * * * *